US009050264B2

(12) United States Patent
Kumar et al.

(10) Patent No.: US 9,050,264 B2
(45) Date of Patent: Jun. 9, 2015

(54) CELLULOSE CAPSULES AND METHODS FOR MAKING THEM

(75) Inventors: Vijay Kumar, Coralville, IA (US); Bhavik Bhatt, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 229 days.

(21) Appl. No.: 13/508,409

(22) PCT Filed: Nov. 8, 2010

(86) PCT No.: PCT/US2010/055859
§ 371 (c)(1),
(2), (4) Date: Jul. 23, 2012

(87) PCT Pub. No.: WO2011/057206
PCT Pub. Date: May 12, 2011

(65) Prior Publication Data
US 2012/0277323 A1    Nov. 1, 2012

Related U.S. Application Data

(60) Provisional application No. 61/259,119, filed on Nov. 7, 2009.

(51) Int. Cl.
| A61K 31/075 | (2006.01) |
| A61K 9/48 | (2006.01) |
| A61K 9/00 | (2006.01) |
| A61K 9/16 | (2006.01) |
| A61K 31/135 | (2006.01) |
| A61K 31/167 | (2006.01) |

(52) U.S. Cl.
CPC ............. *A61K 9/4816* (2013.01); *A61K 9/0024* (2013.01); *A61K 9/1611* (2013.01); *A61K 9/1623* (2013.01); *A61K 9/1641* (2013.01); *A61K 9/485* (2013.01); *A61K 9/4858* (2013.01); *A61K 9/4866* (2013.01); *A61K 31/135* (2013.01); *A61K 31/167* (2013.01)

(58) Field of Classification Search
None
See application file for complete search history.

(56) References Cited

U.S. PATENT DOCUMENTS

| 1,778,096 | A | * | 10/1930 | Voss et al. ................... 424/451 |
| 2,526,683 | A | | 10/1950 | Murphy et al. |
| 2,887,440 | A | | 5/1959 | Greminger et al. |
| 3,909,444 | A | * | 9/1975 | Anderson et al. ........ 428/402.24 |
| 4,001,211 | A | | 1/1977 | Sarkar |
| 4,753,652 | A | | 6/1988 | Langer |
| 4,993,137 | A | | 2/1991 | Muto et al. |
| 5,679,112 | A | | 10/1997 | Levy et al. |
| 5,698,155 | A | | 12/1997 | Grosswald et al. |
| 5,756,123 | A | | 5/1998 | Yamamoto et al. |
| 5,986,168 | A | | 11/1999 | Noishiki |
| 6,254,635 | B1 | | 7/2001 | Schroeder et al. |
| 6,410,050 | B1 | | 6/2002 | Yang |
| 6,436,091 | B1 | | 8/2002 | Harper |
| 6,627,749 | B1 | | 9/2003 | Kumar |
| 6,752,953 | B2 | | 6/2004 | Chen et al. |
| 6,800,753 | B2 | | 10/2004 | Kumar |
| 6,821,531 | B2 | | 11/2004 | Kumar |
| 7,166,464 | B2 | | 1/2007 | McAllister et al. |
| 2001/0025196 | A1 | | 9/2001 | Chinn et al. |
| 2002/0086990 | A1 | | 7/2002 | Kumar et al. |
| 2003/0083741 | A1 | | 5/2003 | Woo |
| 2004/0047909 | A1 | | 3/2004 | Ragheb |
| 2004/0115273 | A1 | | 6/2004 | Sparer et al. |
| 2004/0219185 | A1 | | 11/2004 | Ringeisen |
| 2005/0064038 | A1 | | 3/2005 | Dinh |
| 2005/0131225 | A1 | | 6/2005 | Kumar et al. |
| 2005/0143807 | A1 | | 6/2005 | Pavnick |
| 2005/0228174 | A1 | | 10/2005 | Gillette et al. |
| 2005/0287208 | A1 | | 12/2005 | Kumar et al. |
| 2006/0093672 | A1 | | 5/2006 | Kumar et al. |
| 2006/0193885 | A1 | | 8/2006 | Neething |
| 2006/0265053 | A1 | | 11/2006 | Hunt |
| 2007/0003588 | A1 | | 1/2007 | Chinn |
| 2007/0038295 | A1 | | 2/2007 | Case |
| 2007/0203564 | A1 | | 8/2007 | Rusk |
| 2007/0213801 | A1 | | 9/2007 | Kutryk et al. |
| 2007/0275458 | A1 | | 11/2007 | Gouma |
| 2009/0222085 | A1 | | 9/2009 | Kumar |

OTHER PUBLICATIONS

Kim, Y.J., et al., Fluorometric Assay of DNA in Cartilage Explants Using Hoechst 33258, Anal Biochem (1988) 174: 168-176.
Hoerstrup et al., Functional Living Trileaflet Heart Valves Grown in Vitro, Circulation, (2000) 102(19): 44-49.
Farndale et al., Improved quantitation and discrimination of sulphated glycosaminoglycans by use of dimethylmethylene blue, Biochim Biophys Acta, (1986) 883: 173-177.
G. H. M. Engbers, et al., Blood compatible hemodialysis membranes, Trans. Annual meeting of the Society for Biomaterials and the International Biomaterials Symposium, (1994) p. 109.
J. Morales et al., Plasma modification of cellulose fibers for composite materials, J. Appl. Polym. Sci., (2006); 101:3821-3826.
J. Zhang et al., Chemical modification of cellulose membranes with sulfoammonium zwitterionic vinyl monomer to improve hemocompatibility, Colloids and Surfaces B: Biointerfaces (2003) 30:249-257.
J. Yuan et al., Improvement of blood compatibility on cellulose membrane surface by grafting betaine, Colloids and Surfaces B: Biointerfaces (2003); 30:147-155.
Roy Chowdhury & Kumar, "Fabrication and Evaluation of Porous 2,3-Dialdehydecellulose Membrane as Potential Biodegradable Tissue-engineering Scaffold," J. Biomed. Mater. Res. (2006) 76A: 300-309.
Mol, A., et al., Autologous Human Tissue-Engineered Heart Valves: Prospects for Systemic Application, Circulation (2006), 114 (suppl 1): 1152-1158.

(Continued)

*Primary Examiner* — Jeffrey S. Lundgren
*Assistant Examiner* — Michael Schmitt
(74) *Attorney, Agent, or Firm* — McDonnell Boehnen Hulbert & Berghoff LLP

(57) ABSTRACT

Disclosed are cellulose capsules, methods for preparing a cellulose capsule, and compositions comprising cellulose capsules, including sustained- or controlled-release dosage forms comprising cellulose capsules.

23 Claims, 11 Drawing Sheets

(56) References Cited

OTHER PUBLICATIONS

Thubrikar, M., et al., The Elastic Modulus of Canine Aortic Valves In Vivo and in Vitro, Circ Res. (1980), 47 (5):792-800.

Zioupos, P., et al., Changes in the mechanical properties of bioprosthetic valve leaflets made of bovine pericardium, as a result of long-term mechanical conditioning in vitro and implantation in vivo, J. Mater Sci: Mater Med. (1993), 4(6):531-537.

Bernacca G. M., et al., Hydrodynamic function of polyurethane prosthetic heart valves: influences of Young's modulus and leaflet thickness, Biomaterials, (2002), 2391):45-50.

Huszar et al., Monitoring of Collagen and Collagen Fragments in Chromatography of Protein Mixtures, Anal Biochem, (1980) 105:424-429.

Chandran, K. B., et al., Pulsatile Flow Past Aortic Valve Bioprostheses in a Model Human Aorta, J Biotech, (1984) 17(8):609.

In Kap Ko and Hiroo Iwata, An Approach to Constructing Three-Dimensional Tissue, Annals New York Academy of Sciences, vol. 944 (2006) pp. 443-455.

Entcheva, Emilia, et al., Functional cardiac cell constructs on cellulose-based scaffolding, Biomaterials 25 (2004) pp. 5753-5762.

Sodian, Ralf, MD, et al., Tissue Engineering of Heart Valves: In Vitro Experiences; Ann Thorac Surg 2000; 70:140-44.

Sodian, Ralf, MD, et al., Fabrication of a Trileaflet Heart Valve Scaffold from a Polyhydroxyalkanoate Biopolyester for Use in Tissue Engineering, Tissue Engineering, vol. 6, No. 2, 2000, pp. 183-188.

Millon, L.E and Wan, The Polyvinyl Alcohol-Bacterial Cellulose System As a New Nanocomposite for Biomedical Applications, J. Biomed Mater Res Part B: Appl Biomater, 79B: 245-253 (2006).

Backdahl, H., et al., Mechanical properties of bacterial cellulose and interactions with smooth muscle cells, Biomaterials 27 (2006) 2141-49.

Fries, C.C. and Wesolowski, S.A., The polyester-oxidized cellulose compound vascular prosthesis: A preliminary report, Trans. Amer. Soc. Artif. Int. Organs, vol. X (1964), 227-230.

Pulapura, S. and Kohn, J., Trends in the Development of Bioresorbable Polymers of Medical Applications, J. Biomaterials Applications, vol. 6, pp. 216-250 (1992).

Helenius, G. et al., In vivo biocompatibility of bacterial cellulose, J. Biomed Mater Res Part A, vol. 76A (2005), pp. 431-438.

* cited by examiner

CELLULOSE CAPSULES AND METHODS FOR MAKING THEM

FIELD OF THE INVENTION

The invention relates generally to drug delivery systems, including cellulose-containing capsules, compositions of matter comprising cellulose-containing capsules, sustained/controlled release dosage forms comprising cellulose-containing capsules, and methods for making cellulose-containing capsules.

BACKGROUND OF THE INVENTION

The first two-piece capsule was developed in 1848 and was made from animal-based gelatin, derived primarily from collagen. Capsules are now produced in hard and soft forms, and are common dosage forms for solid, semi-solid, liquid, pellet or herbal preparations primarily in the pharmaceutical and vitamin/health supplement markets. Capsules typically require fewer excipients to produce than tablet dosage forms, and consequently are easier to produce than tablets. They are also easy to swallow and are hence associated with patient compliance.

Currently, gelatin-based hard shell capsules make up a significant proportion of the global pharmaceutical market. Gelatin has high affinity for moisture and is known to react chemically with agents that contain functional groups, such as reducing functionalities (for example, aldehdye groups), which can make gelatin capsule unsuitable for certain drugs. Gelatin capsules are also sensitive to heat and humidity, which affect the usability of the product. Further, because gelatin is an animal-based product, some consumers seek to avoid gelatin-products for religious, cultural, or dietary restrictions, or even because of a perceived risk of contracting spongiform encephalopathy. The more common alternatives to gelatin based capsules are hydroxypropylmethylcellulose and starch capsules. However, these have shown erratic dissolution profiles.

Cellulose is a known natural biostable and biocompatible polymer material. Due to its safe biological characteristics, cellulose has been used in a number of applications. Cellulose has a high mechanical and wet strength, which makes it a good material for coatings, membranes, or barriers for intracorporeal devices (e.g., surgical implants). While cellulose derivatives, such as hydroxypropylmethylcellulose, have been used to prepare capsules and some capsule-based delivery products, these cellulose derivatives are typically soluble in aqueous medium, and require addition of other formulation agents that increase manufacturing complexity and costs. [See, U.S. Pat. No. 6,752,953 (Chen, et al.); U.S. Pat. No. 2,526,683 (Murphy, et al.); U.S. Pat. No. 4,001,211 (Sarkar, et al.); U.S. Pat. No. 4,993,137 (Muto, et al.); U.S. Pat. No. 5,698,155 (Grosswald, et al.); U.S. Pat. No. 6,410,050 (Yang); and U.S. Pat. No. 5,756,123 (Yamamoto, et al.)].

Existing capsule-based delivery technology provides dosage forms with capsule shells that disintegrate or dissolve upon contact with an aqueous medium. Thus, the performance of capsules as an oral delivery system relies primarily upon the specific formulation of the active agent(s) or upon further capsule coating technology. Consequently, improperly formulated capsules can fail and cause undesired release of active agent(s) (e.g., high localized active agent concentrations), which can cause adverse physiological effects in the patient (e.g., GI irritation), or reduce the efficacy of the active agent(s) (e.g., hydrolyzable active agent(s)).

Existing capsule-based delivery technology does not by itself provide sustained- and/or controlled-release of active agents. Additional technology (e.g., coatings) must be used in combination with existing capsule shells in order to modify the inherent delivery profile of the encapsulated active agent(s).

Thus, there is a need to develop a capsule-based drug delivery system that provides good long-term storage stability, is chemically inert with the active agent(s) it contains, is relatively simple and economical to produce, and/or offers easy modifications of its drug release characteristics.

SUMMARY OF THE INVENTION

In some aspects, the invention provides a capsule shell comprising cellulose, wherein the cellulose is present in an amount that is effective to render the capsule shell substantially non-disintegrating/non-dissolving in aqueous media. The capsule shell can, for example, be formed in one or more layers, with at least one layer comprising cellulose in an amount effective to render the capsule shell substantially non-disintegrating/non-dissolving in aqueous media. The one or more cellulose-containing layers can, in certain embodiments, contain additional materials, as described below. Moreover, the capsule shell can include other layers not including cellulose, to provide additional beneficial properties as would be apparent to the person of skill in the art.

In some aspects, the invention provides a cellulose-containing capsule shell having at least one layer consisting essentially of cellulose. For example, the entire cellulose-containing capsule shell can consist essentially of cellulose.

In some aspects, the invention provides a sustained- and/or controlled-release capsule comprising (a) a capsule shell as described herein (e.g., comprising cellulose in an amount that is effective to render the capsule shell non-disintegrating/non-dissolving in aqueous media); (b) one or more active agents (e.g., disposed within the shell); and (c) optionally, one or more optional pharmaceutically acceptable formulation aids (e.g., disposed within the shell).

In some aspects, the invention provides a sustained- and/or controlled-release capsule comprising (a) a capsule shell having at least one layer consisting essentially of cellulose; (b) one or more active agents; and (c) one or more optional pharmaceutically acceptable formulation aids.

In some aspects, the invention provides a method for preparing a cellulose-containing capsule shell comprising (a) providing a methylolcellulose solution; and (b) forming cellulose-containing capsule shells from the methylolcellulose solution. Providing the methylolcellulose solution can, for example, include (a1) providing a source of cellulose; and (a2) treating the cellulose with paraformaldehyde in anhydrous polar aprotic solvent (e.g., dimethylsulfoxide) under conditions suitable to form the methylolcellulose solution.

In some aspects, the invention provides a cellulose-containing capsule shell produced by a method comprising (a) providing a methylolcellulose solution; and (b) forming cellulose-containing capsule shells from the methylolcellulose solution. Providing the methylolcellulose solution can, for example, include (a1) providing a source of cellulose; and (a2) treating the cellulose with paraformaldehyde in anhydrous polar aprotic solvent (e.g., dimethylsulfoxide) under conditions suitable to form the methylolcellulose solution.

In some aspects, the invention provides a sustained- and/or controlled-release dosage form comprising (a) a cellulose-containing capsule shell as described herein; and (b) an active agent, wherein the sustained-release dosage form has a zero-order, an apparent zero-order, and/or a first-order release rate in an aqueous medium.

In some aspects, the invention provides a sustained- and/or controlled-release dosage form comprising (a) a cellulose-containing capsule shell comprising cellulose in an amount of about 50% (w/w) or more; and (b) an active agent, wherein the sustained-release dosage form has a zero-order, an apparent zero-order, and/or a first-order release rate in an aqueous medium.

In some aspects, the invention provides a sustained-release dosage form comprising (a) a cellulose-containing capsule shell having at least one layer consisting essentially of cellulose; and (b) an active agent, wherein the sustained-release dosage form has about a zero-order, an apparent zero-order, and/or a first-order release rate in an aqueous medium.

In some aspects, the invention provides a cellulose-containing capsule shell comprising cellulose and one or more capsule shell permeability modifiers. The one or more capsule shell permeability modifiers can, for example, be provided in the same layer as the cellulose.

In some aspects, the invention provides a cellulose-containing capsule shell comprising cellulose and one or more capsule shell porosity modifiers. The one or more capsule shell porosity modifiers can, for example, be provided in the same layer as the cellulose.

In another aspect, the invention provides a biodegradable capsule shell comprising oxidized cellulose, for example, in an amount that is effective to render the capsule shell biodegradable when implanted in a human. For example, the entire capsule shell can consist essentially of oxidized cellulose. Such capsule shells can be made, for example, by oxidizing the cellulose capsules described herein (e.g., before filling with an active agent).

Other aspects of the invention will become apparent to those of skill in the art in view of the following detailed description.

DETAILED DESCRIPTION

Figure 1:
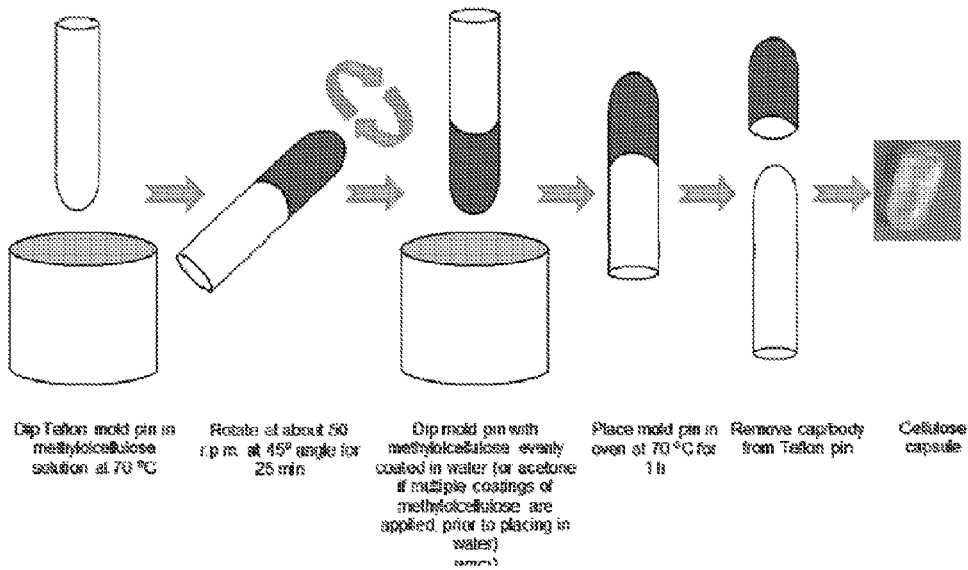
FIG. 1 depicts a general schematic for manufacturing cellulose-containing capsule shells by dip coating pre-fabricated mold pins.

All publications, patent applications, patents and other references mentioned herein, if not otherwise indicated, are explicitly incorporated by reference herein in their entireties for all purposes.

Unless otherwise defined, all technical and scientific terms used herein have the same meaning as commonly understood by one of ordinary skill in the art. In case of conflict, the present specification, including definitions, will control.

The term "capsule" as used herein includes any soft or hard shell capsule (optionally containing medicament). A capsule shell can be a unibody delivery vehicle or comprised of two capsule shell pieces, the longer capsule shell piece is called the body and the smaller capsule shell piece is referred to as the cap, which typically engages with each other as one shell body.

The term "cellulose" as used herein refers to the pure polysaccharide having the formula $(C_6H_{10}O_5)_n$, in a linear chain of $\beta(1 \rightarrow 4)$ linked D-anhydroglucopyranose units, including microcrystalline cellulose and powdered cellulose. The number of D-anhydroglucopyranose units typically ranges from about 50 to about 350 in microcrystalline cellulose, from about 700 to 1000 in powdered cellulose, and from several hundreds to ten thousand or more in cotton, cotton linters, or pulp. Specific reference is made when referring to derivative forms of cellulose (e.g., cellulose ethers, cellulose esters, etc.).

"Active agent" as used herein means any compound, composition of matter or mixture thereof, which provides some pharmaceutical effect when administered to a subject (e.g., vitamins, nutritional supplements, pharmaceutical drugs, biologics, etc.) or render the intended effect when used for non-pharmaceutical applications (agricultural chemicals such as pesticides, fungicides, bactericides, flavors, fragrances, etc.).

The term "dosage form" is taken to mean a composition or device comprising a capsule shell and at least one active agent (e.g., disposed within the shell). Dosage forms can optionally contain inactive ingredients, such as carriers (e.g., pharmaceutically-acceptable carriers), excipients, suspending agents, surfactants, disintegrants, binders, diluents, lubricants, stabilizers, antioxidants, osmotic agents, colorants, plasticizers, and the like, that are commonly used to manufacture dosage forms.

The terms "zero-order," "zero-order kinetics," or "zero-order release rate," all refer to the release rate profile of a capsule or dosage form which is characterized by a rate of release that is independent of the concentration of the active agent.

The terms "apparent zero-order," "apparent zero-order kinetics," or "apparent zero-order release rate," all refer to the release rate profile of a capsule or dosage form which is characterized by a rate of release that is independent of the concentration but dependent on the solubility of the active agent, that is, the active agent concentration in the solution remains constant as the drug released is replaced with more from the undissolved agent.

The terms "first zero-order," "first zero-order kinetics," or "first zero-order release rate," all refer to the release rate profile of a capsule or dosage form which is characterized by a rate of release that is dependent on the concentration of the active agent in the solution.

When an amount, concentration, or other value or parameter is given as a range, or a list of upper and lower values, this is to be understood as specifically disclosing all ranges formed from any pair of any upper and lower range limits, regardless of whether ranges are separately disclosed. Where a range of numerical values is recited herein, unless otherwise stated, the range is intended to include the endpoints thereof, and all integers and fractions within the range. It is not intended that the scope of the disclosure be limited to the specific values recited when defining a range.

When the term "about" is used in describing a value or an end-point of a range, the disclosure should be understood to include the specific value or end-point referred to.

The use of "a" or "an" to describe the various elements and components herein is merely for convenience and to give a general sense of the disclosure. This description should be read to include one or at least one, and reference to the singular also encompasses the plural unless it is obvious that it is meant otherwise.

In a broad sense, certain aspects of the invention provide a cellulose-containing capsule shell that can exhibit a controlled and/or sustained-release profile for active agents, methods for making the cellulose-containing capsule shell, and dosage forms comprising the cellulose capsule shell. The cellulose-containing capsule shell according to certain aspects described herein does not dissolve or disintegrate, but rather hydrates and is insoluble in aqueous solutions, regardless of the physiological pH. Thus, the cellulose-containing capsule shell can be used in combination with a variety of core materials comprising at least one active agent and other optional formulating aids. The cellulose-containing capsule shell can be manufactured to any of a variety of common capsule dimensions and shell thicknesses. The ability to control capsule shell thickness and composition allows for a controlled- and/or sustained-release of capsule contents. The methods for producing the cellulose-containing capsule shell allow for the simple modification of capsule size, the introduction of distinct capsule compartments for use in co-formulations, and for developing immediate release, delayed release, and pulsatile release systems, and thus can be formulated to contain agents that typically cannot be manufactured as a co-formulation. In some embodiments, the cellulose-containing capsule shells can be fabricated such so to have two or more compartments. Each compartment can function as an independent housing for formulations. Their permeability can be altered by coating using different polymers.

Accordingly, in certain embodiments, the invention relates to cellulose-containing capsule shells that unlike common commercially available capsule shells (e.g., hard gelatin capsule shells), neither dissolve nor degrade/disintegrate in aqueous solutions (e.g., in the digestive tract). The cellulose-containing capsule shells of certain embodiments of the invention hydrate when contacted with an aqueous solution. A variety of agents (for example, drugs or drug-excipient mixtures) can be filled into the capsule shell. The drug release rate can, for example, be adjusted by manipulating the capsule shell thickness and composition. Cellulose-containing capsule shells and products comprising the cellulose-containing capsule shells can be manufactured using existing commercial machinery (e.g., capsule filling machines). Current strategies used to achieve a constant or controlled release from capsules rely on the physicochemical properties of the excipients, formulation compositions, and the nature of coating polymers. Such technology increases the complexity and cost associated with manufacturing. Accordingly, the capsules of the present invention can provide advantages over the current state of the art.

While certain cellulose-containing capsule shells described herein comprise cellulose in an amount that is effective to render the capsule non-disintegrating/non-dissolving at physiological pH, in other aspects, the invention provides for conversion of the cellulose capsule shell to a degradable form of cellulose. In certain embodiments according to this aspect, the converted cellulose capsule provides a degradable, time-release delivery system that can be used, for example, for surgical implantation. Accordingly, the converted cellulose-containing capsule shell described herein can also be used as a vehicle for degradable sustained/controlled release delivery, pulsatile delivery, or delayed release delivery.

In certain embodiments, the implantable (e.g., biodegradable) forms of capsule shells can be produced through any method that can oxidize the cellulose of a cellulose-containing capsule shell. In one embodiment, the oxidation method comprises oxidation such as, for example, by contacting the cellulose capsule with gaseous oxidants (e.g., nitrogen oxide gases) or a solution containing one or more oxidants (e.g., hypohalites, periodates, etc.). Such oxidants can be generated by known methods such as, for example, using a mixture comprising phosphoric acid, nitric acid, and sodium nitrite under appropriate conditions (see, U.S. Pat. No. 6,627,749 (which is hereby incorporated herein by reference in its entirety). Typically, the extent of cellulose oxidation increases with longer contact time between the cellulose-containing capsule shell and the oxidant. Also capsule shells comprising a greater amount of oxidized cellulose typically exhibit a faster degradation time (and can be more soluble). Accordingly, aspects of the invention provide for implantable dosage forms that comprise an oxidized cellulose capsule shell, and one or more active agents (e.g., antineoplastic agent), optionally with acceptable formulation excipients. Such dosage forms can be easily produced (e.g., as described herein) and surgically implanted.

Cellulose-Containing Capsule Shell

In one aspect, the invention provides a capsule shell comprising cellulose, wherein the cellulose is present in an amount that is effective to render the capsule shell substantially non-disintegrating/non-dissolving in aqueous medium (e.g., at physiological pH).

In an aspect, the invention provides a capsule shell having at least one layer consisting essentially of cellulose. The at least one layer consisting essentially of cellulose can optionally be combined with other layers (e.g., coatings, as described below). In other embodiments, the capsule shell as a whole consists essentially of cellulose.

In certain embodiments, the capsule shell comprises an amount of cellulose that is about 50% (w/w) of the capsule shell. In certain embodiments, the capsule shell comprises an amount of cellulose that is more than 50% (w/w) of the capsule shell, such as about 60% (w/w) or more of the capsule shell (e.g., about 60%, 65%, 70%, 80%, 85%, 86%, 87%, 88%, 89%, 90%, 91%, 92%, 93%, 94%, 95%, 96%, 97%, 98%, 99%, or 100% (w/w) of the capsule shell). In certain embodiments, the capsule shell comprises cellulose in an amount more than about 70% (w/w); more than about 80% (w/w), more than about 90% (w/w), more than about 95% (w/w), or even more than about 98% (w/w). In certain embodiments, an individual cellulose-containing layer of the capsule shell comprises cellulose in any of the above-listed amounts or ranges.

In some embodiments the capsule shell comprises additional optional components. Such components can be provided as part of a cellulose-containing layer (e.g., as a mixture of polymers); and/or provided as a separate layer. Examples of additional components include: (1) cellulose derivatives including, but not limited to, non-enteric cellulose esters (e.g., cellulose nitrate, cellulose acetates, and cellulose triacetate), enteric cellulose esters (e.g., cellulose acetate phthalate, cellulose acetate trimellitate, and hydroxypropyl methylcellulose phthalate), and cellulose ethers (e.g., methyl cellulose, ethyl cellulose, hydroxypropyl cellulose, and hydroxypropyl methylcellulose); (2) polymers/copolymers of acrylate or acrylate derivatives including, but not limited to, polyacrylate, polymethylacrylate, poly(acrylate-methylacrylate), poly(methacrylate-methylmethacrylate), poly(ethylacrylate-methylmethacrylate), poly(ethylacrylate-methylmethacrylate-trimethylammonioethylmethacrylate chloride), and poly(ethylacrylate-methylmethacrylate-trimethylammonioethylmethacrylate chloride); (3) polyolefins including, but not limited to, polyethylene, polypropylene, and polybutylene; (4) vinyl polymers including, but not limited to, poly(vinyl pyrrolidones), polyvinyl chloride, polyvinyl acetate, poly(vinyl acetate phthalate)—an enteric polymer, polyvinyl alcohol, polystyrene and polyacrylonitrile. Additionally, polymer such as poly(ethylene glycols), poly(2-ethyl-2-oxazoline), alginates and other natural and derived polysaccharides can also be used for making the capsule. In certain embodiments (e.g., those in which the capsule is made using certain methods described herein), the optional components can be soluble in/miscible with polar aprotic solvents such as dimethylsulfoxide, and can be added in amounts sufficient to alter porosity or the permeability properties of the capsule shell. Thus, in some embodiments when a particular application may benefit from modifying the solubility and release profile of the capsule shell (e.g., in a "fast-release" delivery formulation such as, for example, pain medications), such modifications can be achieved through the addition of optional components, in amounts that can be determined by those of skill in the art.

Plasticizers that can be used optionally in forming the cellulose capsule include, but are not limited to, glycerine, propylene glycol, polyethylene glycol (PEG 200-6000), diethyl phthalate, dibutyl phthalate, dibutyl sebacate, triethyl citrate, acetyltriethyl citrate, acetyltributyl citrate, tributyl citrate, triacetyl glycerine, castor oil, acetylated monoglyceride, coconut oil, and the like.

Optional additives such as colorants and pigments can be included in the capsule shell as desired.

The cellulose included in the cellulose-containing capsule shell can be derived from any variety of cellulose sources known in the art such as, for example, cotton linter, purified cotton, paper, α-cellulose, purified wood pulp, microcrystalline cellulose, powdered cellulose, cellulose modified to other polymers, and/or similar materials as known in the art, or mixtures thereof [see, e.g., U.S. Pat. Nos. 6,627,749; 6,821,531; and 6,800,753; and Published U.S. Patent Application Nos: 2002/0086990; 2005/0131225; 2005/0287208; and 2006/0093672, each of which is hereby incorporated by reference herein in its entirety].

Capsule sizes can be varied considering various factors for any particular application, such as dosage or route of administration. Standard capsule sizes are known in the art, and for oral dosage forms typically range from size 5 (volume of 0.1 mL) to size 000 (volume of 1.37 mL). The cellulose-containing capsule can be manufactured to a variety of capsule shell thicknesses. The ability to control capsule shell thickness allows for a controlled- and/or sustained-release of capsule contents (active agents and soluble excipients). As the structural integrity of cellulose-containing capsule shell is maintained in aqueous solutions (the cellulose hydrates upon contacting aqueous medium, but does not dissolve/disintegrate), the drug release characteristic of the cellulose-containing capsule varies depending on the capsule shell thickness and composition.

The capsule shells of the invention retain mechanical strength when dry or when contacted with an aqueous solution, particularly at physiological pH. Accordingly, in certain embodiments, the capsule shells comprise cellulose in an amount effective to retain the inherent mechanical strength of cellulose. Mechanical strength can be measured by any technique known in the art, such as measurement of tensile strength. The assessment of the mechanical strength of the cellulose shell can be made with reference to a standard, such as a cellulose film or a series of cellulose films comprising various percentages of cellulose.

In certain embodiments, dosage forms comprise a cellulose-containing capsule shell containing distinct compartments that can be used, for example, in manufacturing co-formulations comprising multiple active agents. In certain embodiments, dosage forms comprising the cellulose capsule shell can comprise a capsule shell contained within another capsule shell. In certain embodiments both capsules comprise the cellulose-containing capsule shell described herein. In some embodiments one capsule is a cellulose-containing capsule shell as described herein, and one capsule is a standard capsule shell (e.g., shells comprising for example, gelatin, hydroxypropylmethylcellulose, etc.). In one embodiment, the dosage form comprising the cellulose-containing capsule dosage form within a standard capsule dosage form provides an immediate release, followed by a sustained release. Thus, embodiments provide for dosage forms that can provide an array of release profile combinations (quick-release, sustained-release and/or controlled-release) as well as an array of active agent co-formulations and combinations.

In certain embodiments, the cellulose-containing capsule shell can be adapted for use as a floating drug delivery system (FDDS) for sustained- and/or controlled-release in the gastric system of a subject. Such systems are generally known in the art (see, e.g., Arora, S., et al., *AAPS PharmSchiTech*, (2005); 6(3):E372-E390, which is hereby incorporated herein by reference in its entirety).

As noted above, another aspect of the invention is a biodegradable capsule shell comprising oxidized cellulose, for example in an amount that is effective to render the capsule shell biodegradable when implanted in a human. For example, the entire capsule shell, or at least one layer thereof can consist essentially of oxidized cellulose. Such capsule shells can be made, for example, by oxidizing the cellulose capsules described herein (e.g., before filling with an active agent). In certain embodiments, the oxidized cellulose is oxidized to provide carboxylate centers (e.g., in a range of 1-30% of the sugar resides). In another embodiment, the oxidized cellulose is oxidized to provide aldehyde centers (e.g., in a range of 1-30% of the sugar residues). Of course, a mixture of carboxylate and aldehyde centers can be provided by oxidation. In certain embodiments, the oxidized cellulose has a degree of polymerization of 82 or less, and a degree of crystallinity of 38% or less, as described in U.S. Pat. No. 6,627,749. The oxidized cellulose-containing capsules can further include other materials and layers, generally as described above with respect to the cellulose-containing capsule shells. Another aspect of the invention is an implantable dosage form comprising (a) a biodegradable capsule shell as described above; (b) one or more active agents; and (c) optionally, a pharmaceutically acceptable formulation agent.

Capsule Shell Fabrication

In one aspect, the invention provides a method for preparing a cellulose-containing capsule shell, comprising (a) providing a source of cellulose; (b) solubilizing the cellulose with one or more solvents under conditions suitable to form cellulose (or a derivative thereof) liquid solution; and (c) forming the cellulose-containing capsule shell from the cellulose liquid solution.

In one embodiment, the liquid solution comprises methylolcellulose. In one embodiment, step (b) of the method comprises treating the cellulose with paraformaldehyde in anhydrous polar aprotic solvent (e.g., dimethylsulfoxide, DMF, dimethylacetamide) under conditions suitable to form a methylolcellulose solution. Thus, in one embodiment the method comprises (a) providing a source of cellulose; (b) treating the cellulose with paraformaldehyde in anhydrous polar aprotic solvent under conditions suitable to form a methylolcellulose solution; and (c) forming cellulose-containing capsule shells from the methylolcellulose solution.

In another aspect, the invention provides a method for preparing a cellulose-containing capsule, comprising (a) providing a methylolcellulose solution; and (b) forming cellulose-containing capsule shells from the methylolcellulose solution. Providing the methylolcellulose solution can, for example, include (a1) providing a source of cellulose; and (a2) treating the cellulose with paraformaldehyde in anhydrous polar aprotic solvent under conditions suitable to form the methylolcellulose solution.

The liquid solution can contain an amount of cellulose or methylolcellulose, and optionally one or more cellulose derivatives or other polymers or agents that are soluble or dispersible in the solvent, such that the solution allows for the fabrication of the desired cellulose-containing layers of the capsule shells (e.g., as described herein). The characteristics of the solution, such as cellulose or methylolcellulose content and identity and content of any other polymers or agents can be optimized by one of skill in the art based on the particular fabrication technique to be employed and the desired composition and properties of the layer to be fabricated. Various solution characteristics can be taken into consideration such as, for example, viscosity and flow properties when preparing the liquid solution. In certain embodiments, the amount of cellulose, methylolcellulose or cellulose derivative in the liquid solution is from about 0.5% to about 9.0% (w/w). In some embodiments the amount of cellulose or cellulose derivative in the liquid solution is from about 1.0% to about 6.5% (w/w). In certain embodiments the amount of cellulose, methylolcellulose or cellulose derivative in the liquid solution is from about 1.0% to about 6.1% (w/w). In yet other embodiments, the amount of cellulose, methylolcellulose or cellulose derivative in the liquid solution is from about 1.0% to about 4.5% (e.g., 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, or 4.5%). When the cellulose-containing layer is to include another component (e.g., another cellulose derivative or a poly(meth)acrylate as described above), that component can be provided in the liquid solution as well. The person of skill in the art can select solvents and concentrations to ensure co-solubility or co-dispersability of all components of the layer to be fabricated.

The formation of the cellulose-containing capsule shell from the liquid solution can be accomplished using standard capsule fabrication methods (e.g., dip coating technique) and adapted as needed to allow for any particular specifications required for the ultimate use of the capsule shell. In some embodiments, the method comprises applying one or more coats of the coating solution onto a rod or pin by dipping, followed by rotating the coated pin, and subsequently regeneration of cellulose in the capsule form (FIG. 1). In certain embodiments, the method comprises a non-sticky rod or pin of appropriate dimensions that is dipped in the liquid coating solution and rotated for a period of time that allows for uniform application and spreading of the solution. When methylolcellulose (or some other hydrolysable cellulose derivative) is used, it can then be converted back to cellulose by exposure to water (e.g., before filling with active agent). The water hydrolyzes the methyl groups of the methylolcellulose, substantially returning the cellulose to its native chemical state. The regenerated cellulose is insoluble in water, and so will create a capsule shell that is substantially non-disintegrating/non-dissolving in aqueous media. Accordingly, in certain embodiments, the forming step (b) includes forming a layer of methylolcellulose, then converting the methylolcellulose to cellulose by exposing it to water. After cellulose regeneration, it can be cured, for example, by heating. In case of multiple dip coatings, after each coating and rotation steps the pin is immersed in a volatile organic solvent such as acetone that serves as a non-solvent for a period until the applied methylolcellulose solution solidifies. The coating process is repeated until a desired coating thickness is obtained. The cellulose regeneration and curing processes are then followed. Any additional layers can be formed using methods familiar to the person of skill in the art.

The physical characteristics of the cellulose-containing capsule shell can be adjusted based on the number of times the non-adhesive pin (capsule mold) is dipped in the solution during the manufacturing process. For example, with progressive dip coating steps, the cellulose-containing capsule shell exhibits increased thickness, opacity, and rigidity (or decreased flexibility).

In any of the above-described method for producing cellulose-containing capsule shells, the capsule shell forming molds/pins can be made of any kind of material that is chemically inert with cellulose. Optionally the material can be selected to be non-sticky such as, for example, stainless steel, ceramic, or Teflon.

While particular conditions for forming methylolcellulose solutions can be determined by one of skill in the art, in certain embodiments the formation of methylolcellulose from a cellulose source is performed at a temperature in the range of from about 100° C. to about 160° C., while in other embodiments the temperature range is from about 100° C. to about 145° C. In some embodiments, the treating step (b) is performed at a temperature in the range of from about 120° C. to about 130° C. (See, e.g., U.S. Pat. No. 6,800,753, which is hereby incorporated herein by reference in its entirety). In certain embodiments methylolcellulose solutions are stored under dry conditions.

In certain embodiments, the methylolcellulose solution can be used to produce unibody capsule shells. The procedure involves coating the mold pin made up of a water soluble substance such as gelatin or hydroxypropylmethylcellulose and conform to the desired capsule geometry and size, with the methylolcellulose solution and subjecting the coated mold to similar fabrication steps as used for the two shell piece capsules (vide supra).

Of course, in certain embodiments, other capsule fabrication techniques known in the art; and other methods of cellulose processing known in the art can be used to create the capsule shells and capsules of the present invention.

Sustained and/or Controlled-Release Dosage Form

The capsule shells described above can be used to form sustained- and/or controlled-release dosage forms. For example, in one aspect, the invention provides a sustained- and/or controlled-release capsule dosage form comprising a capsule shell comprising cellulose, wherein the cellulose is present in an amount that is effective to render the capsule shell substantially non-disintegrating/non-dissolving in aqueous media, irrespective of the pH, as described herein.

In one aspect, the invention provides a sustained- and/or controlled-release capsule dosage form comprising a cellulose-containing capsule shell having at least one layer consisting essentially of cellulose. For example, in certain embodiments, the cellulose-containing capsule shell consists essentially of cellulose. Of course, in other aspects, the cellulose-containing layer includes other components, as described above.

In certain embodiments, the sustained- and/or controlled-release dosage form releases an effective amount of active agent to the patient over a prolonged period of time, and can provide for less frequent dosing (e.g., once-a-day dosing) than for immediate release compositions. In some embodiments, the sustained-release formulation can be advantageously used for highly soluble drugs, oils, or other active agents that are typically difficult to deliver in a sustained-release formulation. In general, active agent(s) from cellulose capsules release in three stages: an initial phase that exhibits rapid or delayed release depending on the diffusion rate of the core agent from the saturated shell or equilibration of the continuous phase and/or core agent(s) with the shell or its pores; an intermediate (apparent) zero-order release phase; and a final first-order phase. Factors such as solubility of the core agent(s), concentration gradient between the inside and outside of the capsule shell, and/or the porosity of the shell, diffusibility of the core material(s) through the shell matrix may affect the release rate during the (apparent) zero-order phase. The duration of the (apparent) zero-release amount, on the other hand, depends on the amount of the active agent, in the core and the rate of release.

In certain embodiments, active agents include any physiologically or pharmacologically active substance that produces a localized or systemic effect or effects in animals, including warm blooded mammals, (e.g., humans, domestic animals, farm animals, and the like). Active agents include, for example, organic or inorganic water-soluble or water-insoluble small molecule pharmaceuticals, proteins, enzymes, enzyme inhibitors, hormones, polynucleotides, nucleoproteins, polysaccharides, glycoproteins, lipoproteins, and polypeptides.

Representative non-limiting classes of water-soluble and water-insoluble drugs or nutritional agents include those falling into the following therapeutic categories: ACE-inhibitors; anti-anginal drugs; anti-arrhythmias; anti-asthmatics; anti-cholesterolemics; anti-convulsants; anti-depressants; anti-diarrhea preparations; anti-histamines; anti-hypertensive drugs; anti-infectives; anti-inflammatory agents; anti-lipid agents; anti-manics; anti-nauseants; anti-stroke agents; anti-thyroid preparations; anti-tumor drugs; anti-tussives; anti-uricernic drugs; anti-viral agents; acne drugs; alkaloids; amino acid preparations; anabolic drugs; analgesics; anesthetics; angiogenesis inhibitors; antacids; antiarthritics; antibiotics; anticoagulants; antiemetics; antiobesity drugs; antiparasitics; antipsychotics; antipyretics; antispasmodics; antithrombotic drugs; anxiolytic agents; appetite stimulants; appetite suppressants; beta blocking agents; botanical substances, bronchodilators; cardiovascular agents; cerebral dilators; chelating agents; cholecystokinin antagonists; chemotherapeutic agents; cognition activators; contraceptives; coronary dilators; cough suppressants; decongestants; deodorants; dermatological agents; diabetes agents; diuretics; emollients; enzymes; erythropoietic drugs; expectorants; fertility agents; fungicides; gastro-intestinal agents; growth regulators; hormone replacement agents; hyperglycemic agents; hypnotics; hypoglycemic agents; laxatives; migrain treatments; mineral supplements; mucolytics; narcotics; neuroleptics; neuromuscular drugs; non-steroidal anti-inflammatory drugs (NSAIDS); nutritional additives; peripheral vaso-dilators; polypeptides; prostaglandins; psychotropics; renin inhibitors; respiratory stimulants; steroids; stimulants; sympatholytics; thyroid preparations; tranquilizers; uterine relaxants; vaginal preparations; vaso-constrictors; vertigo agents; vitamins; wound healing agents.

Non-limiting examples of specific active agents which may be useful in the present invention can be chosen from the list which follows. Mixtures of these agents and their salts used for appropriate therapies are also contemplated: acetaminophen; acetylsalicylic acid and its buffered form; albuterol and its salts; alkaline phosphatase; allantoin; aloe; aluminum acetate, carbonate, chlorohydrate, hydroxide-alprozolam; amino acids; aminobenzoic acid; amoxicillin; ampicillin; ansacrine; amsalog; anethole; ascorbic acid; aspartame; aspirin; atenolol; bacitracin; BCNU (carmustine) beclomethasone dipropionate; benzocaine; benzoic acid; benzophenones; bethanechol; biotin; bisacodyl; bornyl acetate; bromopheniramine maleate; buspirone; caffeine; calcium carbonate; casinate and hydroxide; camphor, captopril; cascara sagrada; castor oil; cefaclor, cefadroxil; cephalexin;

cetylalcohol; cetylpyridinium chloride; chelated(?) minerals; chloramphenicol; chlorcyclizine hydrochloride; chlorhexidine gluconate; chloroxylenol; chloropentostatin; chlorpheniramine maleate; cholestyramine resin; choline bitartrate; chondrogenic stimulating protein; cirnetidine hydrochloride; cinnamedrine hydrochloride; citalopram; citric acid; cod liver oil; codeine and codeine phosphate; clonidine and its hydrochloride salt, clorfibrate; cortisone acetate; ciprofloxacin HCl; cyanocobalamin; cyclizine hydrochloride; danthron; dexbrompheniranime maleate; dextromethorphan hydrobromide; diazepam; dibucaine; diclofenac sodium; digoxin; diltiazem; dimethicone; dioxybenzone; diphenhydramine citrate; diphenhydramine hydrochloride; docusate calicurn, potassium and sodium; doxycycline hyclate; doxylamine succinate; efaroxan; enalpril; enoxacin; erythromycin; estropipate; ethinyl estradiol; ephedrine; epinephrine bitartrate; erythropoictin; eucalyptol; ferrous fiamarate, gluconate and sulfate; folic acid; fosphenyloin; 5-fluorouracil (5-FU) fluoxetine HCl; furosemide; gabapentan; gentarnicingemfibrozil; glipizide; glycerin; glyceryl stearate; griseofulvin; growth hormone; guaifenesin; hexylresorcinol; hydrochlorothiaxide; hydrocodone bitartrate; hydrocortisone and its acetate; 8-hydroxyquinoline sulfate; ibuprofen; indomethacin; inositol; insulin; iodine; ipecac-, iron; isoxican; ketamine; lactic acid; lecithin; leuprolide acetate; lidocaine and its hydrochloride salt; lifinopril; liotrix; lovastatin; luteinizing hormone; LHRH (luteinizing hormone releasing hormone); magnesium carbonate, hydroxide, and salicylate; trisilocate; mefenamic acid; meclofenanic acid; meclofenamate sodium; medroxyprogesterone acetate; methenamine mandelate; menthol; meperidine hydrochloride; metaproterenol sulfate; methyl nicotinate; methyl salicylate; methsuximide; metronidazole and its hydrochloride; metoprolol tartrate; miconazole nitrate; minoxidil; morphine; naproxen and its sodium salt; nifedipine; neomycin sulfate; niacin; niacinamide; nicotine; nicotinamide; nitroglycerin; nonoxynol-9; norethindone and its acetate; nystatin; omega-3 polyunsaturated fatty acids; omeprazole; oxolinic acid; oxybenzone; oxtriphylfine; para-aminobenzoic acid (PABA); padimate 0; paramethadoine; pentastatin; peppermint oil; pentaerythriol tetranitrate; pentobarbital sodium; pheniramine maleate; phenobarbital; phenol; phenolphthalein; phenylephrine hydrochloride; phenylpropanolamine and its hydrochloride salt; phenyloin; phenelzine sulfate; pirmenol; piroxicam; polymycin B sulfate; potassium chloride, nitrate and other soluble inorganic salts; prazepam; procainamide hydrochloride; procaterol; propoxyphene and its hydrochloride salt; propoxyphene napsylate; pramiracetin; pramoxine and ita hydrochloride salt propronolol hydrochloride; pseudoephedrine hydrochloride and sulfate; pyridoxine; quinapril; quinidine gluconate and sulfate; quinestrol; ralitoline; ranitidine; resorcinol; riboflavin; salicylic acid; sesame oil; shark liver oil; simethicone; sodium bicarbonate; citrate and fluoride; sodium monofluorophosphate; sucralfate; sulfanethoxazole; sulfasalazine; sulfur; tacrine and its hydrochloride salt; theophylline; terfenidine; thioperidone; trimethrexate; triazolam; timolol maleate; tretinoin; tetracycline hydrochloride; tolmetin; tolnaftate; triclosan; triprolidine hydrochloride; undecylenic acid; vancomycin; verapamil hydrochloride; vidaribine phosphate; vitamins A, B, C, D, B1, B2, B6, B12, E, K; witch hazel; xylometazoline hydrochloride; zinc; zinc sulfate; zinc undecylenate.

In certain embodiments the active agent is effective in the treatment of angina pectoris such as the non-limiting examples of coronary vasodilators (e.g., ACE inhibitors, nitroglycerin), blood pressure medications and heart rate reducing agents (e.g., statins), nitrates, beta-blockers (e.g., carvedilol, propranolol, atenolol), calcium antagonist/calcium-channel blockers (e.g., nifedipine and amlodipine), isosorbide mononitrate and nicorandil, and other therapeutic agents known in the art.

In one embodiment the active agent comprises one or more compounds that are typically difficult to formulate and/or deliver such as, for example, hydrolysable compounds, hygroscopic compounds, oils, and the like.

In one embodiment further modifications in the sustained-release dosage form can be achieved using pharmaceutically acceptable carriers and/or excipients well known in the art. Such carriers and/or excipients can be mixed with the active agent and filled in the cellulose-containing capsule shell. As described herein, the capsule shells and the dosage forms comprising the capsule shells do not require special formulation (e.g., coatings, etc.) for sustained-release. As demonstrated by the illustrative Examples below, and the description above, the cellulose-containing capsule shells can provide an inherent sustained release profile, which can be manipulated for any particular application through the addition of optional components, or through modifications of the shell.

The preparation and formulation of pharmaceuticals for oral use are known in the art and include, for example, combining active agents with any solid carriers and/or excipients and processing the resultant mixture of granules (optionally, after grinding) to obtain capsule core material. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose and cellulose derivatives, such as microcrystalline cellulose, methylcellulose, hydroxypropylmethylcellulose, cellulose acetates, or sodium carboxymethylcellulose; gums, including arabic and tragacanth; and proteins, such as gelatin and collagen. If desired, the active agent can be combined with disintegrating or solubilizing agents, such as the cross-linked polyvinylpyrrolidone, agar, and alginic acid or a salt thereof, such as sodium alginate.

The capsules can be sealed by any method known in the art. In certain embodiments, the capsule can be sealed by simple mechanical joining (one shell diameter is designed to snugly fit within the diameter of the mating shell). In certain embodiments, the capsule seal comprises a chitosan-based adhesive, methylolcellulose solution, or any other acceptable adhesives using standard sealing techniques. In some embodiments the capsule seal is made by a banding or a spray sealing mechanism. The capsules can further be coated with, for example, a seal coating, an enteric coating, an extended release coating, a targeted delayed release coating, a film coating, a barrier coating, or an enzyme degradable coating. Consequently, the invention allows for the design and manipulation of the inherent sustained-release profile of the cellulose-containing capsule shells, and accordingly be modified to incorporate profiles including immediate release, controlled release, extended release, delayed release, targeted release, synchronized release, or targeted delayed release. Multi-compartment capsule shells can also be utilized for multi-stage release or pulsatile release of one or more than one active agent. Different active agents can be mixed or separated in different compartments such that they can be released at different stages or released according to different profiles. Multiple coatings can be applied for a desired performance.

The capsule shells can be filled with active agent formulation (e.g., granules, powder, liquid, suspension, etc.) using conventional techniques and filling machines.

As described herein, the capsule of the invention can comprise optional coating layers, either to the capsule shell itself, or to the active agent core. Such coatings can be applied immediately outside the core, either a drug-containing core or a drug-layered core, by conventional coating techniques such as pan coating or fluid bed coating using solutions of polymers in water or suitable organic solvents or by using aqueous polymer dispersions. Suitable materials for the coating include cellulose derivatives such as hydroxyethylcellulose, hydroxypropylcellulose, hydroxypropylmethylcellulose, poly(vinylpyrrolidone), polyvinylpyrrolidone/vinyl acetate copolymer, ethyl cellulose aqueous dispersions, and the like. Coating levels can be determined by those of skill in the art depending on the particular application. Optionally, coating solution may contain one or more agents, such as colorants, and plasticizers.

Common enteric coating layers can be applied onto the active agent cores with or without seal coating by conventional coating techniques, such as pan coating or fluid bed coating using solutions of polymers in water or suitable organic solvents or by using aqueous polymer dispersions. Enteric polymers are known in the art and include the non-limiting examples of cellulose acetate phthalate, cellulose acetate trimellitate, hydroxypropylmethylcellulose phthalate, poly(vinyl acetate phthalate), carboxymethylethylcellulose, and co-polymerized methacrylic acid/methacrylic acid methyl esters.

Oxidized cellulose-containing capsule shells can similarly be filled and sealed to provide biodegradable dosage forms.

Other Applications

While the above disclosure details the cellulose technology in terms of shells, capsules, and dosage forms, the technology finds broad applications in various commercial areas. For example, the cellulose "shells" can be formed to accommodate sizes for controlled- or sustained-release applications in industrial, agricultural, or household use. For example, cellulose shells can be sized and manufactured for any application in which sustained-release is desired and can include any compounds and compositions that are chemically compatible with cellulose such as, for example, fragrances, perfumes, fertilizing agents, poisons, herbicides, pesticides, fungicides, antibacterial agents, industrial or household cleaning agents, cleansing agents, personal grooming compositions, or the like.

It will be apparent to those of skill in the art that while the various aspects and embodiments of the invention as described herein provide advantages over existing capsule technology, the invention nevertheless can be used in combination with any existing formulation technology known in the art.

The following Examples are merely illustrative of certain embodiments of the invention, which is defined by the appended claims. Accordingly, the Examples should not be considered limiting to the scope of the invention.

EXAMPLES

Example 1

Preparation of Methylolcellulose Solution

General schemes for preparing cellulose solutions are known to those of skill in the art. The following method describes non-limiting method conditions for generating a methylolcellulose solution from cotton linter starting material. Briefly, cellulose (cotton linter) can be converted into a methylolcellulose solution by reacting cotton linter with paraformaldehyde in anhydrous dimethylsulfoxide at 120-140° C. for 4-6 h. In a typical experiment, pieces of cotton linters (50 g, cut to about 1 cm×1 cm) were dried in an oven at 70-80° C. for 24 h. In a three-neck 1000 mL round bottom flask, equipped with a condenser and a thermometer, about 500 mL of DMSO was added and heated to 105° C. for 4 h. The oven-dried cotton linters (about 24 g) were then added to the DMSO and allowed to soak for about 2 h at 105° C. The temperature was then raised to 125° C. and 60 g of paraformaldehyde was then added in portions. The heating at 125° C. was continued for a period until a clear, viscous solution of methylolcellulose (MC) was formed. The latter was transferred to a dry glass bottle with a lid. Because methylolcellulose solution is highly sensitive to moisture (moisture causes methylolcellulose to regenerate into cellulose), the solution was stored under dry conditions.

Example 2

Preparation of Cellulose-Containing Capsule Shells

Figure 2A:
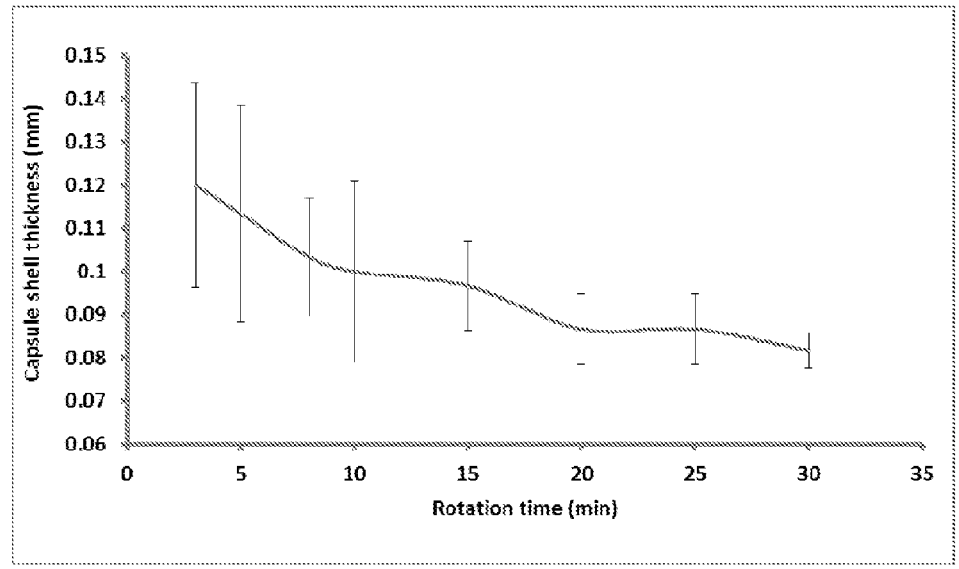
FIGS. 2A-C depict the capsule shell thickness as a function of rotation time after one dip coating with various methylolcellulose solutions containing (A) 4.4%, (B) 3.3%, and (C) 2.2% cellulose content, on a dry weight basis (w/w).
Figure 2B:
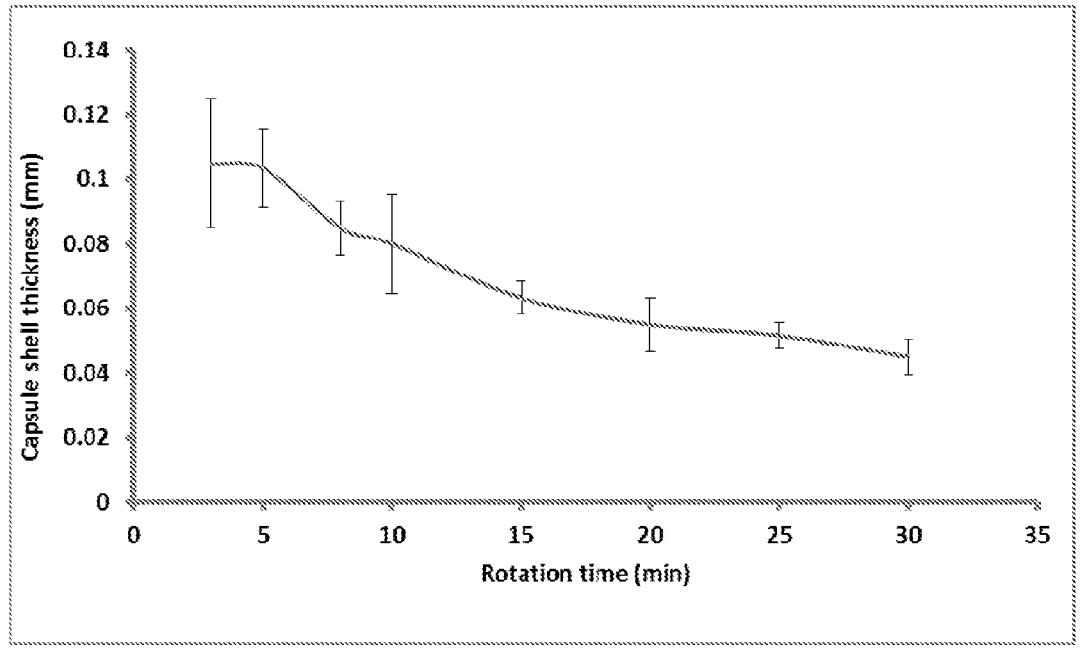
Figure 2C:
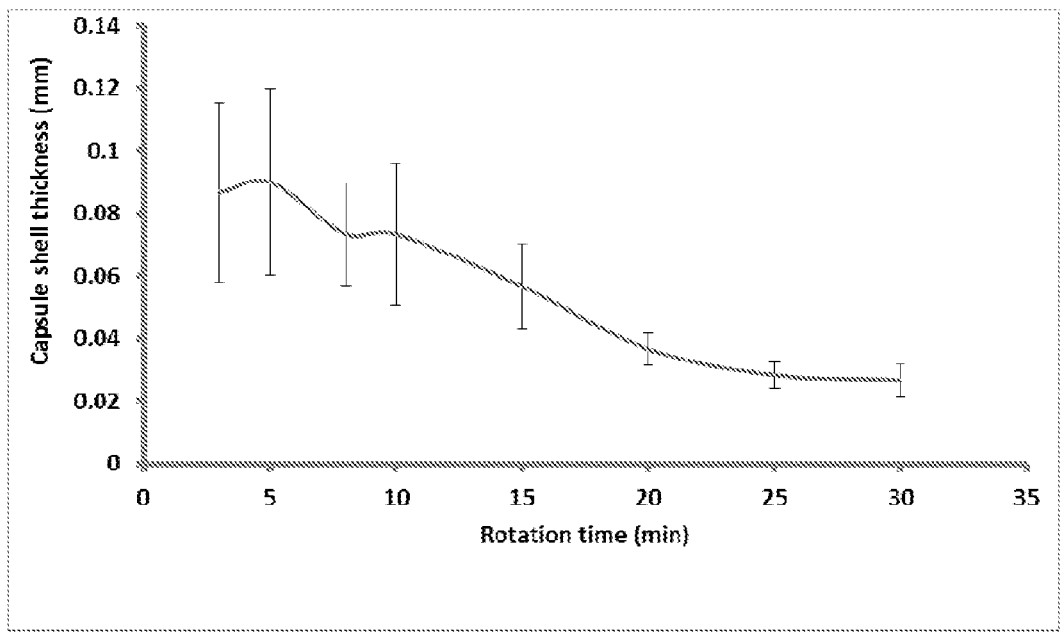
Figure 3A:
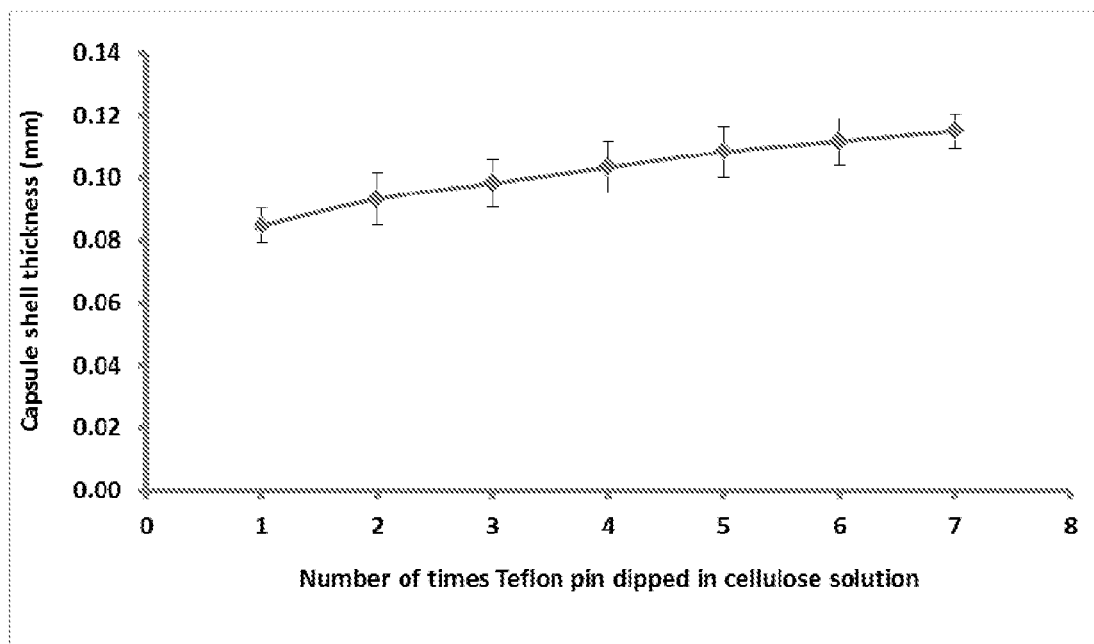
FIGS. 3A-C depict cellulose capsule shell thickness as a function of the number of times the pin was dip coated with methylolcellulose solution having (A) 4.4%, (B) 3.3%, and 2.2% w/w cellulose content (post-dipping rotation time: 30 min.).
Figure 3B:
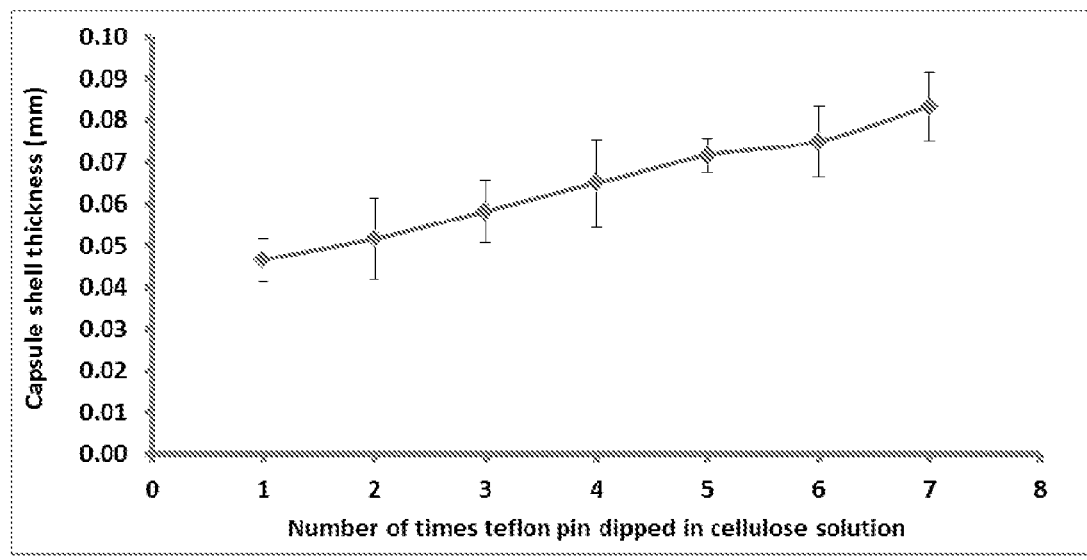
Figure 3C:
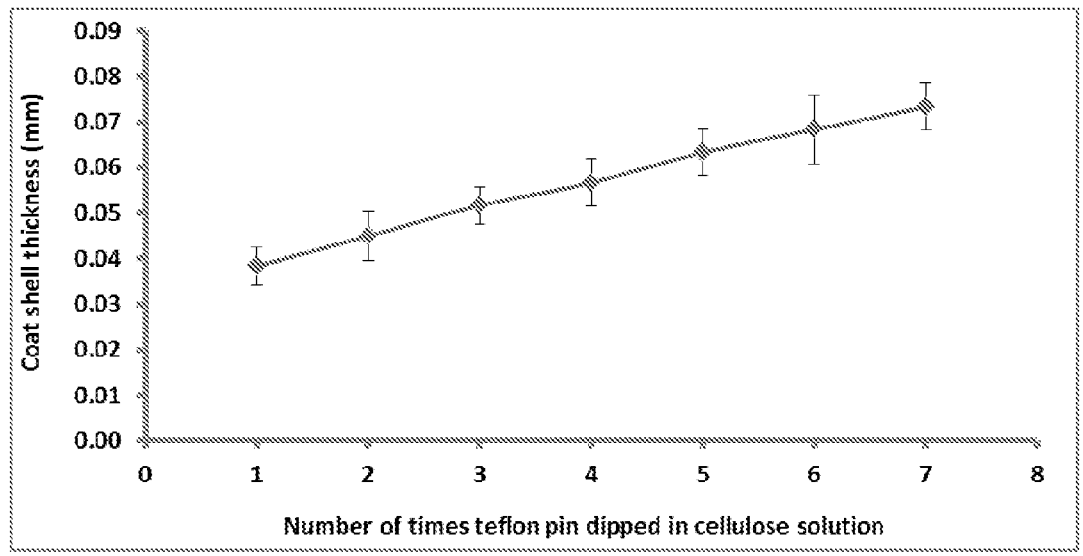

Methylolcellulose solutions containing 2.2, 3.3 and 4.4% w/w cellulose contents, on a dry weight basis, were prepared from cotton linter by treatment with paraformaldehyde in dimethylsulfoxide according to Example 1. Capsule shells were fabricated by dipping the Teflon pins of dimensions 8.0 mm×10 cm (capsule body) and 8.3 mm×10 cm (capsule cap) in the methylolcellulose solution for about 30 sec, and subsequently rotating the pins at a 45° angle at 50±5 r.p.m. for 5 to 45 min in air. The coated pin was placed in acetone (20.0 mL) for about 10 min and then air dried. The dipping and rotating steps were repeated 2-7 times. The coated Teflon pins were then immersed in deionized water (1.5 L) for about 24 h. The capsule shells were then cut to the desired length and cured at 70° C. for 1 h. After curing, the shells were removed from the pins, and stored in a dry container. See, FIG. 1. With one coating, the capsule shell thickness decreased with increasing rotation time. See, FIG. 2A-C; after 30 min. of rotation, the shell thickness of capsules prepared from the three methylolcellulose solutions (containing 2.2, 3.3, and 4.4% cellulose content) were 0.02, 0.05, and 0.08 mm, respectively. FIG. 3A-C shows the increase in shell thickness with an increase in number of times the Teflon pin was coated with the methylolcellulose solution; after 7 coatings and 30 min of rotation, the shell thicknesses of the capsules prepared from the three solutions were 0.07, 0.08 and 0.12 mm, respectively.

Appropriate amounts of methylolcellulose solution and Eudragit S100 (Evonik Rohm GmbH, Kirschenallee, Darmstandt, formerly Rohm Pharm, Weiterstadt, Germany), corresponding to the cellulose:Eudragit S100 concentrations of 97.3:2.7 and 90:10 (%, w/w), were thoroughly mixed, optionally at 45-75° C. for a period until a clear solution was formed. Capsule shells were then made according to Example 2.

Example 3

Release Properties of Cellulose Capsule Shells

Figure 4A:
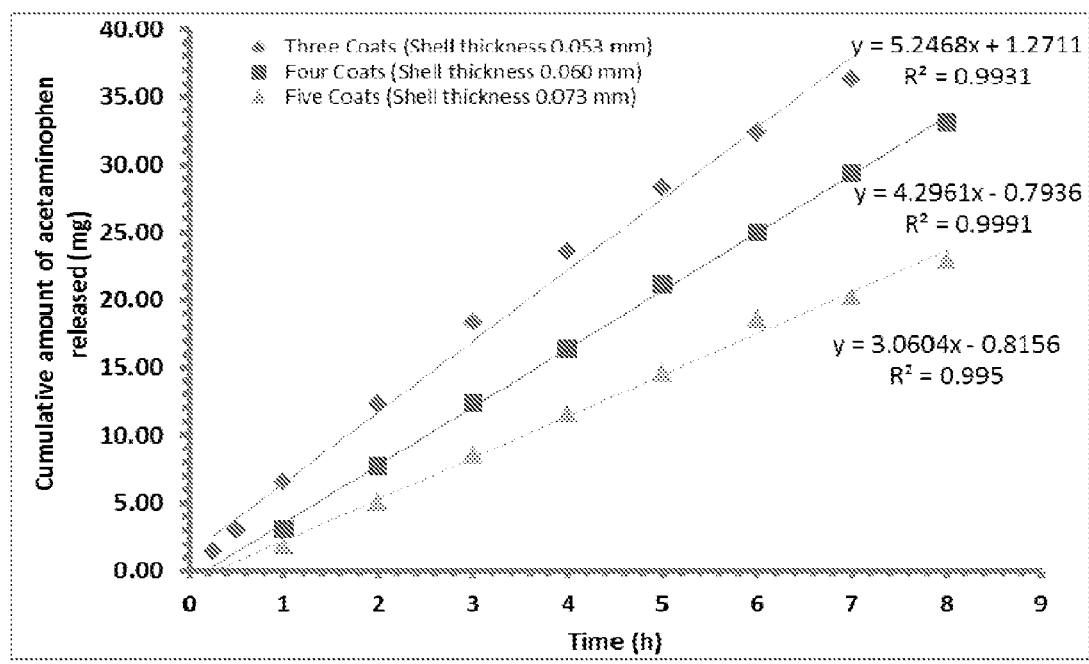
FIG. 4A depicts the acetaminophen release profile from a cellulose capsule loaded with 200 mg of a 3:1 (w/w) mixture of lactose and acetaminophen as a function of capsule shell thickness. Data for a capsule shell thickness of 0.073 mm are represented by triangles (▲); data for a shell thickness of about 0.060 mm are represented by squares (■); and data for a capsule shell thickness of 0.053 are represented by diamonds (♦). The linear fits for each of the capsules are: $y=5.2468x+1.2711$, $R^2=0.9931$ (shell thickness about 0.053 mm); $y=4.2961x-0.7936$, $R^2=0.9991$ (shell thickness about 0.060 mm); $y=3.0604x-0.8156$, $R^2=0.995$ (shell thickness about 0.073 mm).
Figure 4B:
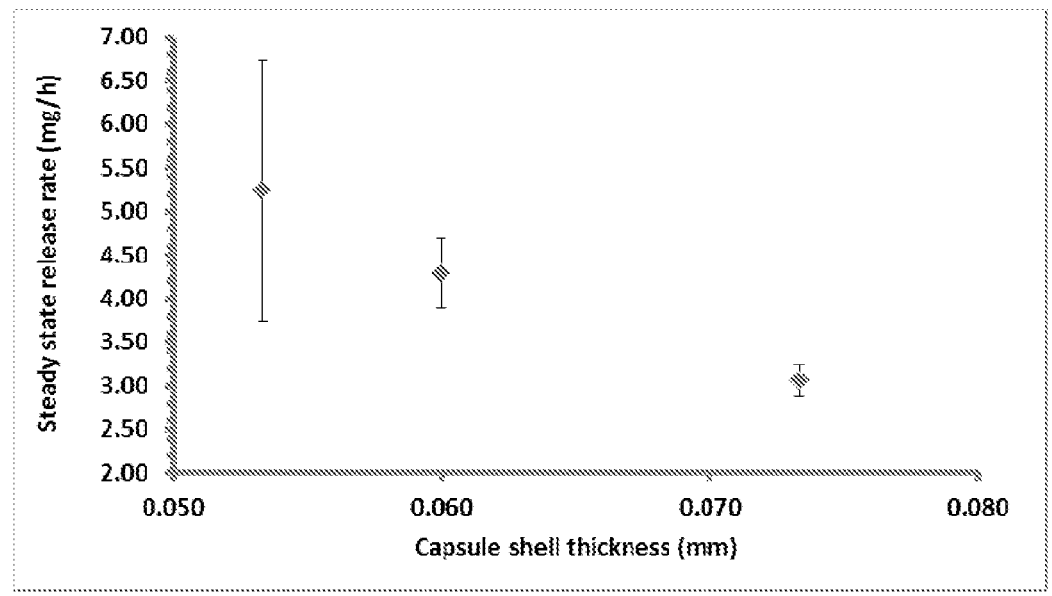
FIG. 4B shows the relationship between capsule shell thickness and the release rate of acetaminophen.

Cellulose capsule shells of three different shell thicknesses (0.05, 0.06 and 0.07 mm) were prepared from the methylolcellulose solution (cellulose content 4.4%, w/w) according to Example 2. They were filled with a homogeneously mixed powder blend of acetaminophen (50 mg) and lactose (150 mg). The dissolution study was performed in water (900 mL) at 37±0.5° C. and 100±2 r.p.m. using a Hansen Research USP II basket apparatus (Hansen Research Corp., Chatsworth, Calif.). The amount of drug released was determined by high performance liquid chromatography (HPLC) using an absolute calibration method and a fully automated Shimadzu LC-6A high performance liquid chromatograph, equipped with a C18 analytical column (Supelco—Sigma Aldrich, Bellefonte, Pa.). The drug was eluted with a 1:3 methanol: water mixture at a flow rate of 0.5 mL/min and detected at a wavelength of 243 nm. The release of acetaminophen increased linearly with time (see FIG. 4A). The release rates, which were 5.25, 4.30, and 3.06 mg/h, respectively, decreased with increasing the shell thickness. See FIG. 4B.

Figure 5:
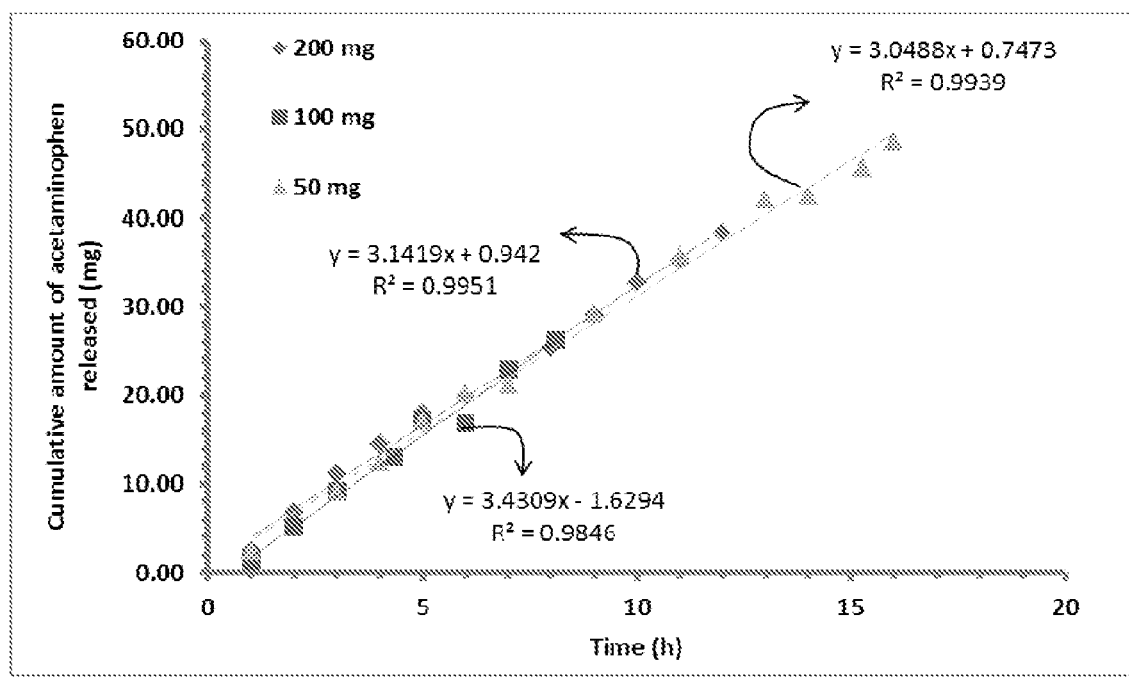
FIG. 5 depicts the effect of drug loading on its release from a cellulose capsule (capsule shell thickness about 0.053 mm). Data for a capsule loaded with 50 mg acetaminophen are represented by triangles (▲); data for a capsule loaded with 100 mg acetaminophen are represented by squares (■); and data for a capsule loaded with 200 mg acetaminophen are represented by diamonds (♦). The linear fits for each of the capsules are: $y=3.1419x+0.942$, $R^2=0.9951$ (drug loading 200 mg); $y=3.4309x-1.6294$, $R^2=0.9846$ (drug loading 100 mg); $y=3.0488x+0.7473$, $R^2=0.9933$ (drug loading 50 mg). The similar slope values obtained for the three drug loadings suggest that the different drug loadings studied have no effect on the release rates.

Cellulose capsule shells (shell thickness 0.07-0.10 mm) prepared according to Example 2 were filled with 50, 100 and 200 mg of acetaminophen. The release studies were carried out in purified water (900 mL) at 37±0.5° C. and 100±2 r.p.m. The amount of acetaminophen released over time was determined by HPLC using conditions described above. The steady-state release rates were 3.05, 3.43 and 3.15 mg/h, respectively. See FIG. 5. These results suggest that drug release rate is independent of drug loaded in the capsule.

Figure 6A:
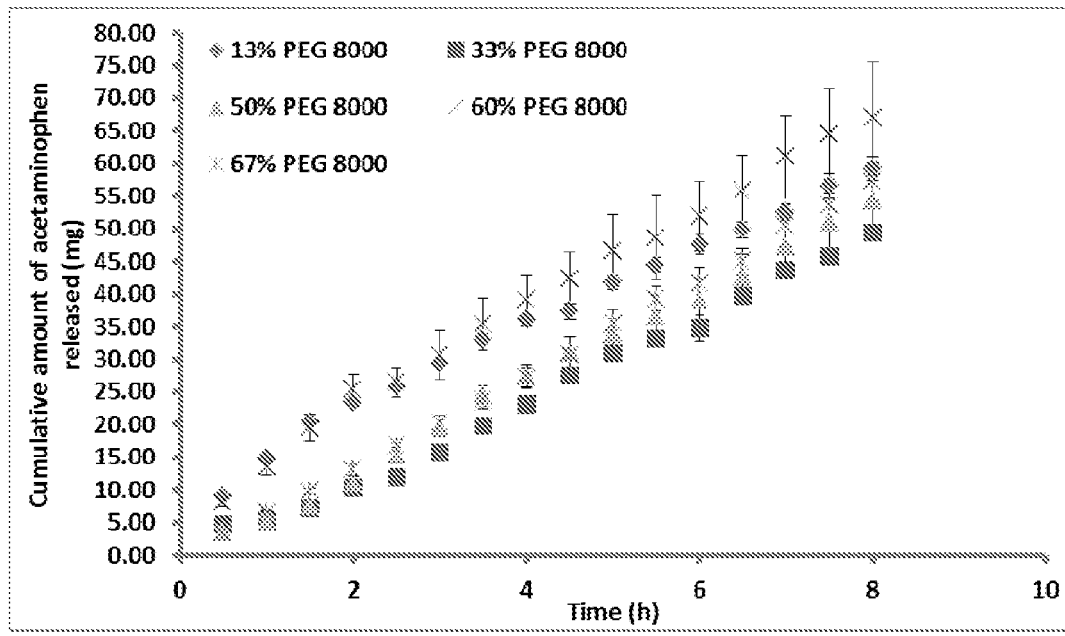
FIG. 6A depicts the release profiles of acetaminophen from cellulose capsules (shell thickness 0.07-0.1 mm) with different amounts of polyethylene glycol 8000 (PEG 8000) in the core.
Figure 6B:
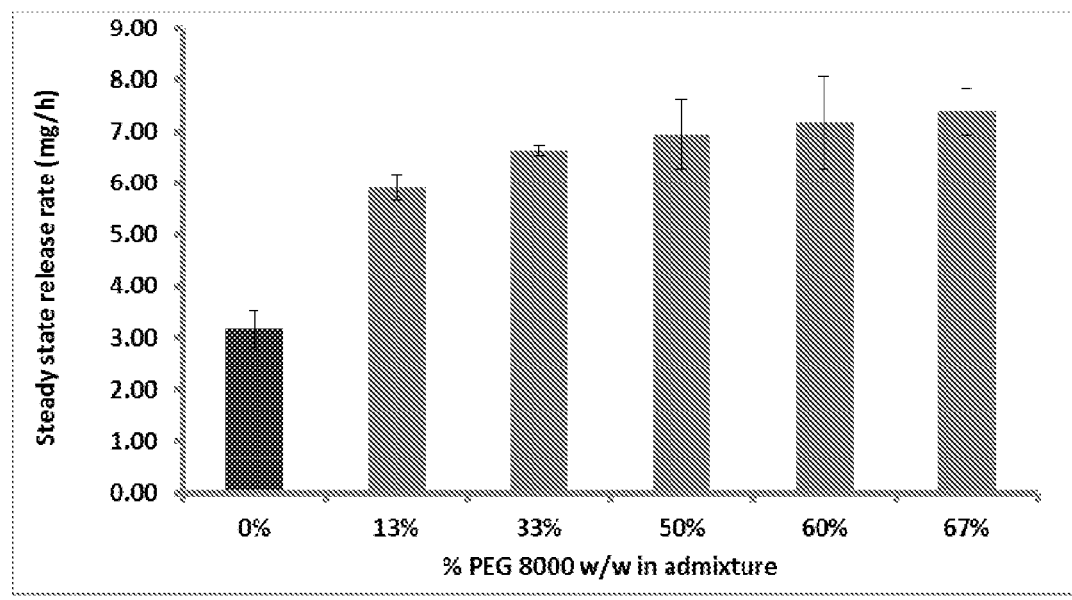
FIG. 6B compares the steady-state release rate of acetaminophen from cellulose capsules as a function of the amount of PEG in the capsule core.

Cellulose capsule shells (shell thickness 0.07-0.10 mm), prepared according to Example 2, were filled with a homogeneously mixed powder blend of acetaminophen (100 mg) and 15, 50, 100, 150, or 200 mg of polyethylene glycol (PEG) 8000 (corresponding to the percent weight ratio of 87:13, 67:33, 50:50, 40:60, or 33:67, respectively, for the total powder fill in the capsule). The release studies were performed in purified water (900 mL) at 37±0.5° C. and 100±2 r.p.m. using the Hansen Research USP II basket apparatus (Hansen Research Corp., Chatsworth, Calif.). The amount of acetaminophen released was determined by HPLC as described above. The release results are presented in FIG. 6A. The steady-state release rates calculated from the linear portion of the curves in FIG. 6A were 5.92, 6.62, 6.95, 7.17, and 7.38 mg/h for capsules comprising 87:13, 67:33, 50:50, 40:60, and 33:67 (% w/w) acetaminophen:PEG 8000 mixtures, respectively. See FIG. 6B. The statistical comparison of the release data suggest that as the amount of PEG increased from 13% to 50% (ANOVA, F>$F_{crit}$ at $\alpha$=0.05, p=0.07). Above 60% w/w PEG 8000 in the formulation, there was no change in the release rate compared to the rate at 50% PEG in the mixture.

Figure 7A:
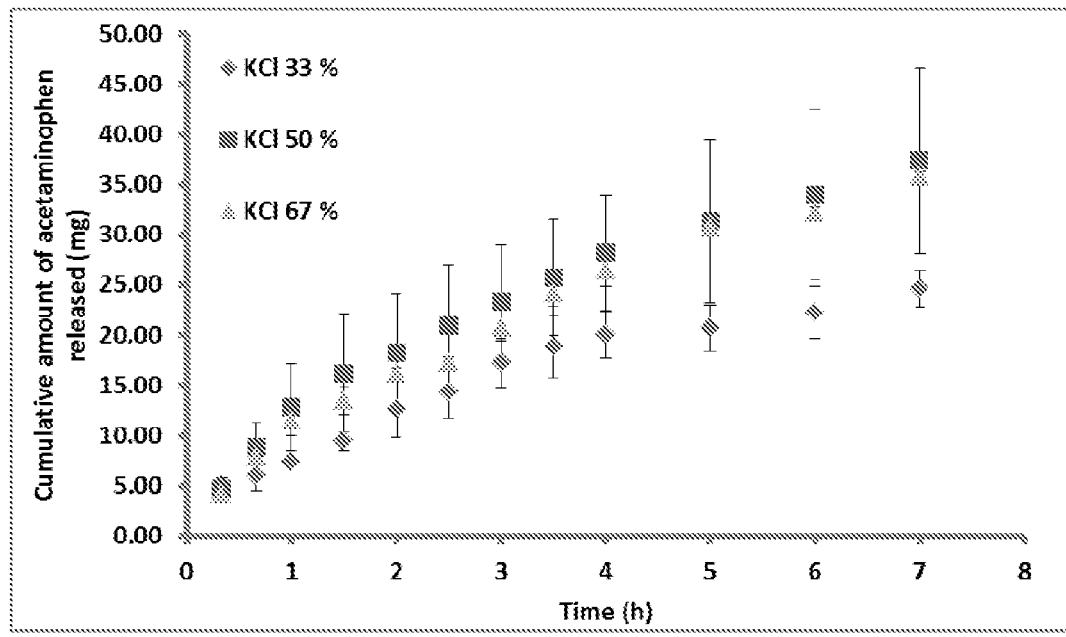
FIG. 7A illustrates the release profiles of acetaminophen from cellulose capsules (shell thickness 0.07-0.1 mm) with different amounts of KCl in the capsule core.
Figure 7B:
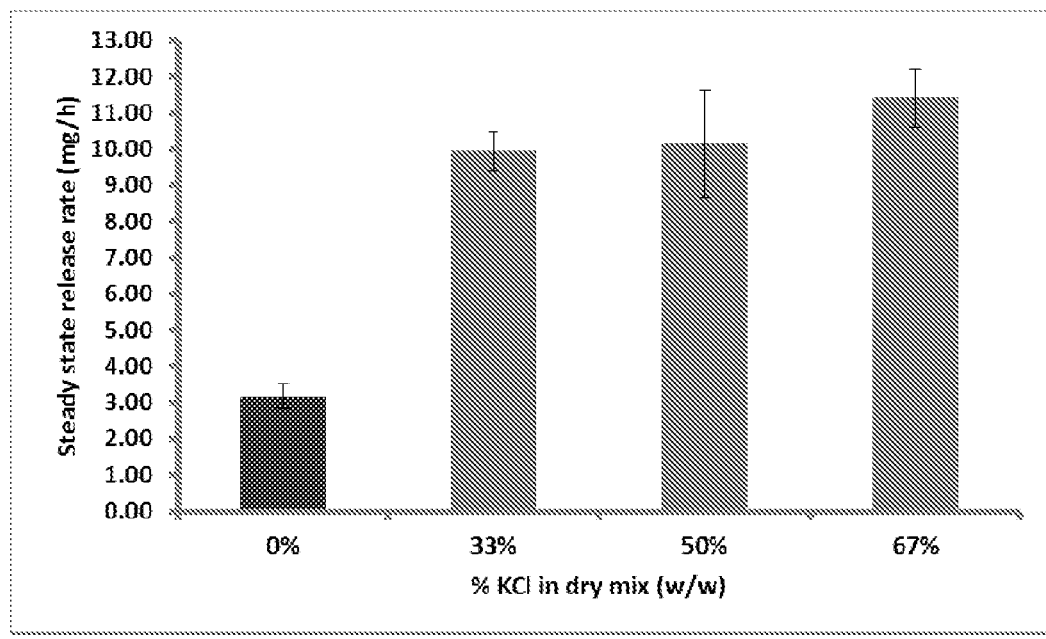
FIG. 7B compares the steady-state release rate of acetaminophen from cellulose capsules as a function of the amount of potassium chloride (KCl) in the capsule core.

Cellulose capsule shells (shell thickness 0.07-0.1 mm) prepared according to Example 2 were filled with acetaminophen (100 mg) and 50, 100 and 200 mg potassium chloride (KCl) (corresponding to the weight ratio of 33:67, 50:50 or 67:33, respectively, for the total powder fill in the capsule). The amounts of acetaminophen released at different times were determined by HPLC, following the procedure described above. The release profiles of acetaminophen are presented in FIG. 7A. The steady-state release rates obtained from the linear portion of the curves presented in FIG. 7A were 9.94, 10.14, and 11.41 mg/h for the 33:67, 50:50, and 67:33 acetaminophen:KCl mixtures, respectively. See FIG. 7B. The ANOVA test results revealed no significant difference between the values, suggesting that increasing the amount of KCl in the capsule has no effect on the acetaminophen release rate.

Figure 8:
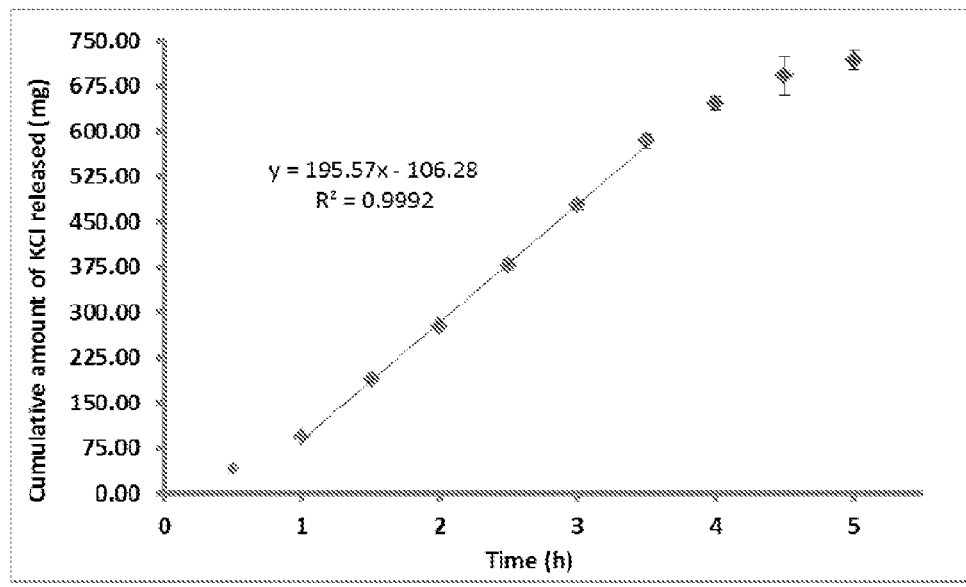
FIG. 8 shows the release of KCl from cellulose capsules (shell thickness 0.07-0.1 mm).

Cellulose capsule shells (shell thickness 0.07-0.10 mm) prepared according to Example 2 were filled with potassium chloride (KCl) (750 mg) and subjected to the dissolution test in water (1000 ml) at 37±0.5° C. and 100±2 r.p.m. using a Hansen Research USP II basket apparatus (Hansen Research Corp., Chatsworth, Calif.). The amount of KCl released over time was analyzed using a potassium ion selective electrode connected to Orion model 420 pH meter Orion model 420, Fisher Scientific, Inc., Pittsburgh, Pa.). The release of KCl from cellulose capsules is shown in FIG. 8.

Figure 9A:
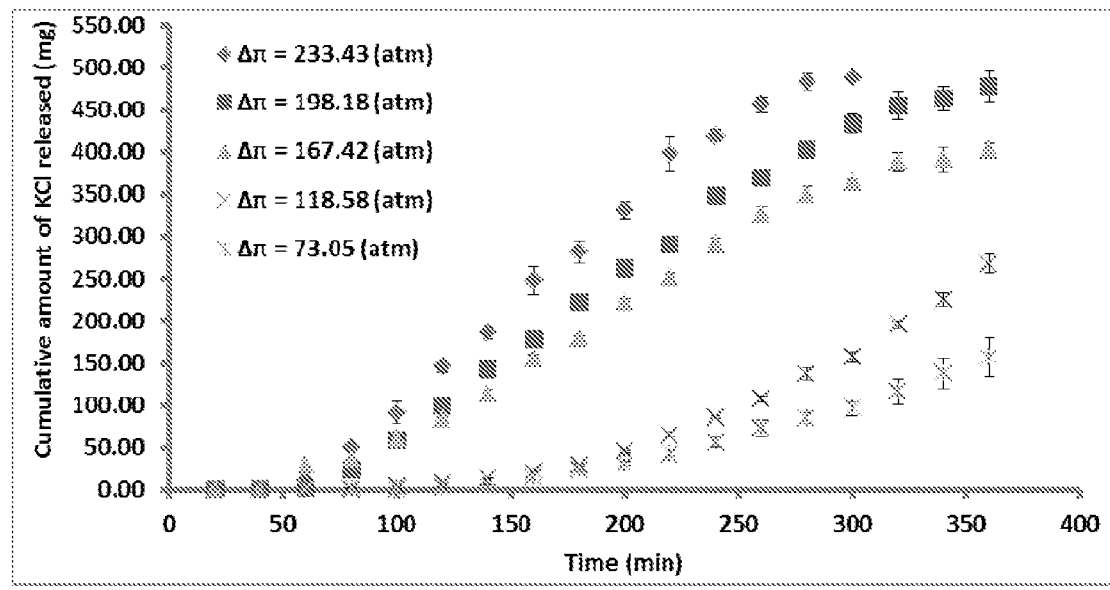
FIG. 9A depicts the release of KCl from cellulose capsules (shell thickness 0.07-0.1 mm) in aqueous urea solutions (conc. 0, 1.5, 3, 5.5, and 8 M corresponding to the osmotic pressure difference of 233.43, 198.43, 167.42, 118.58 and 73.05 atm, respectively, across the capsule shell).
Figure 9B:
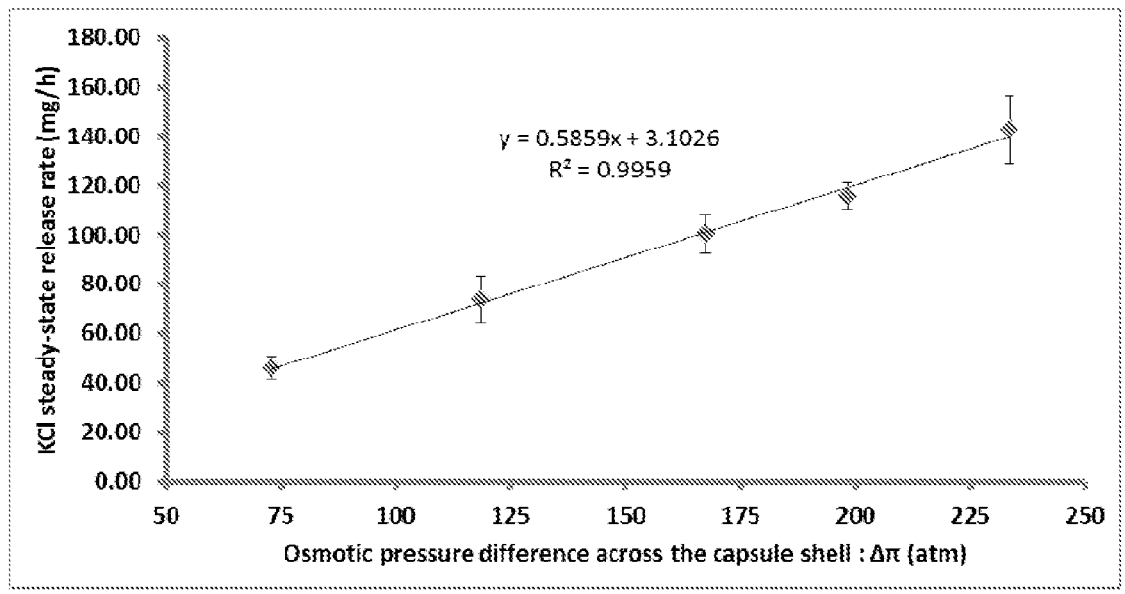
FIG. 9B depicts relationship between the steady release rate of KCl and osmotic pressure difference across the capsule shell.

Cellulose capsule shells (shell thickness 0.07-0.10 mm), prepared according to Example 2, were filled with KCl (500 mg) and subjected to the release study in the unstirred dissolution medium (200 mL) containing 0.0, 1.5, 3.0, 5.5, or 8.0 M urea at 37±0.5° C. using a Hansen Research USP II basket apparatus (Hansen Research Corp., Chatsworth, Calif.). The amount of KCl released was analyzed using a potassium ion selective electrode connected to a pH meter (Orion model 420, Fisher Scientific, Inc., Pittsburgh, Pa.). The release of KCl from cellulose capsules is shown in FIG. 9A. The steady state release rates were 142.8, 115.8, 100.2, 73.8 and 46.2 mg/h in 0.0, 1.5, 3.0, 5.5, and 8.0 M aqueous urea solutions, respectively. FIG. 9B shows a direct relationship between the release rate and the osmotic pressure difference across the capsule shell, suggesting that the release of KCl from the cellulose capsules follows an osmotic mechanism.

Figure 10A:
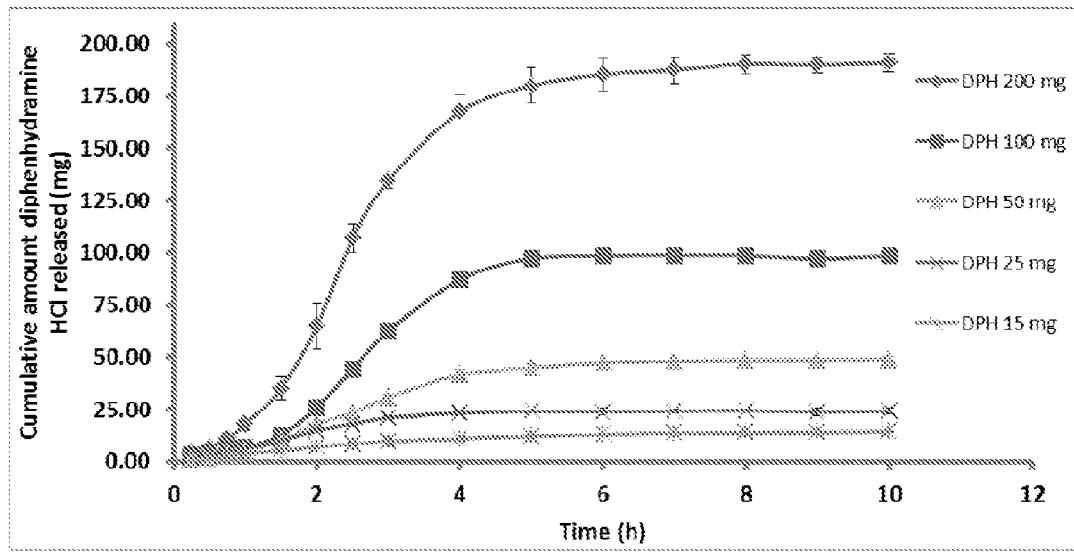
FIG. 10A depicts the release profiles of different amounts of diphenhydramine hydrochloride enclosed (together with lactose) within the capsule core.
Figure 10B:
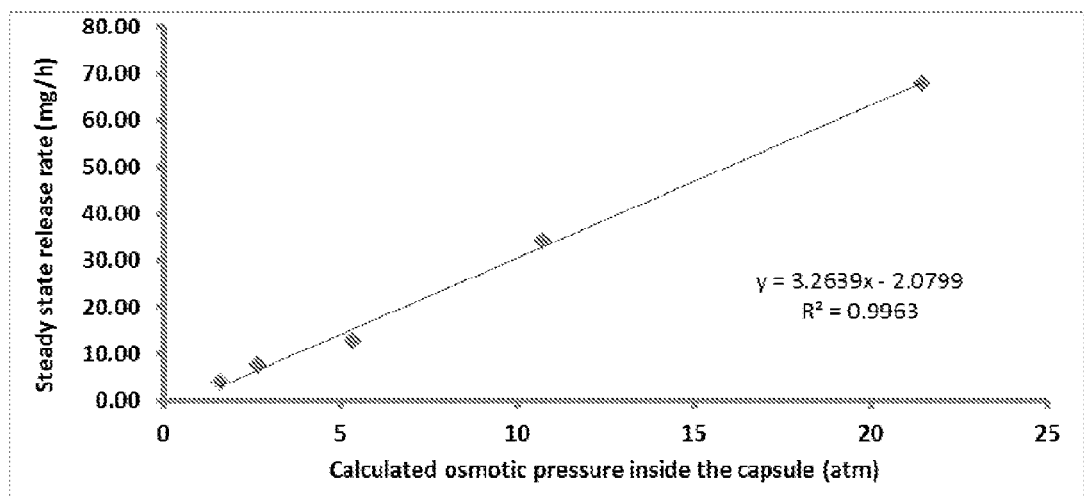
FIG. 10B shows a linear relationship between the steady-state release rates of different amounts of diphenhydramine hydrochloride enclosed and the calculated osmotic pressure inside the capsule.

Cellulose capsule shells (shell thickness 0.07-1.0 mm), prepared according to Example 2, were filled with diphenhydramine hydrochloride and lactose (400 mg) mixed in different weight-by-weight ratios (50:50, 25:75, 12.5:87.5, 6.25:93.75 or 3.75:96.25 weight ratios of diphenhydramine hydrochloride and lactose, respectively). The release study was performed in water (900 mL) at 37±0.5° C. and 100±2 r.p.m. using a Hansen Research USP II basket apparatus (Hansen Research Corp., Chatsworth, Calif.). The amount of drug released was determined by HPLC using a fully automated Shimadzu LC-10A high performance liquid chromatograph, equipped with a C18 analytical column (Supelco). The drug was eluted with a 1:4 (v/v) mixture of methanol:water (containing 1% triethylamine and 2% glacial acetic acid) at a flow rate of 0.2 mL/min and detected at a wavelength of 256 nm. The steady-state release rates of diphenhydramine hydrochloride were 67.96, 34.17, 12.70, 7.58 and 3.92 mg/h for 50:50, 25:75, 12.5:87.5, 6.25:93.75 and 3.75:96.25 diphenhydramine hydrochloride:lactose core powder mixtures. See FIG. 10A. The steady state release rates mentioned above depended linearly with the calculated osmotic pressure developed inside the capsule shell. See FIG. 10B.

Figure 11:
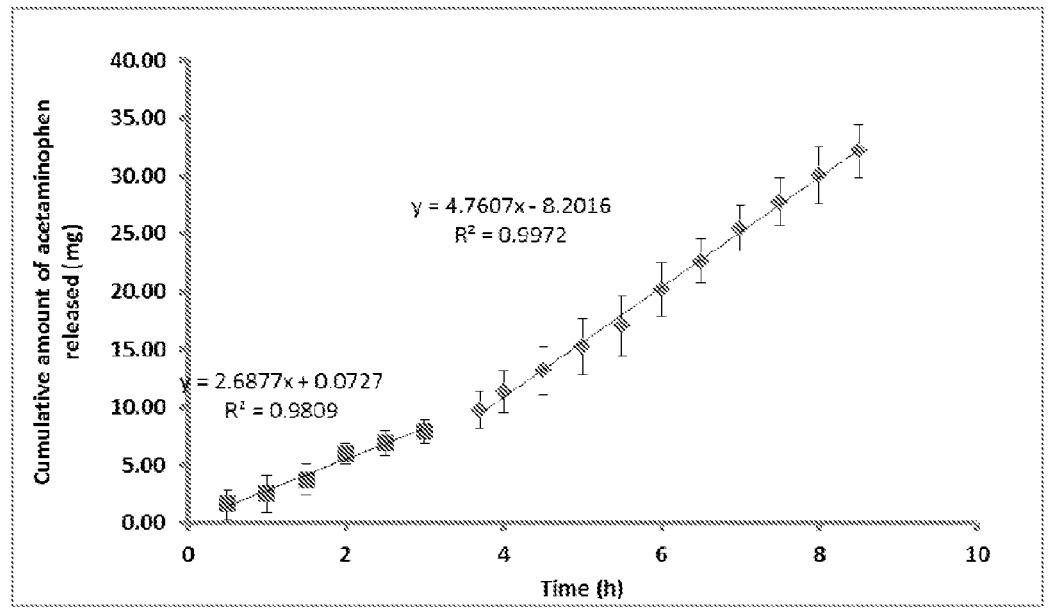
FIG. 11 shows the release of acetaminophen from cellulose:Eudragit 5100 (90:10, % w/w) capsule shells in pH 3 (squares) and pH 7.4 (squares) buffer solutions.

Cellulose:Eudragit (90:10%, w/w) capsule shells (shell thickness~0.08 mm) prepared according to Example 2 were filled with a homogeneously mixed powder blend of acetaminophen (50 mg) and anhydrous lactose (150 mg) and subjected to dissolution study first in pH 3.0 phthalate buffer (900 mL) for 3 h at 37±0.5° C. and 100±2 r.p.m followed by in pH 7.4 phosphate buffer (900 mL) for 5 h at 37±0.5° C. and 100±2 r.p.m. using a Hansen Research USP II basket apparatus (Hansen Research Corp., Chatsworth, Calif.). The amount of drug released was determined by HPLC according to the method described above. The steady-state release rates of acetaminophen in pH 3.0 and 7.4 were 2.68 mg/h and 4.76 mg/h, respectively. See FIG. 11. The higher steady-state release rate observed for acetaminophen at pH 7.4 is attributed to the dissolution of Eudragit, causing the capsule shell to become more porous.

Figure 12:
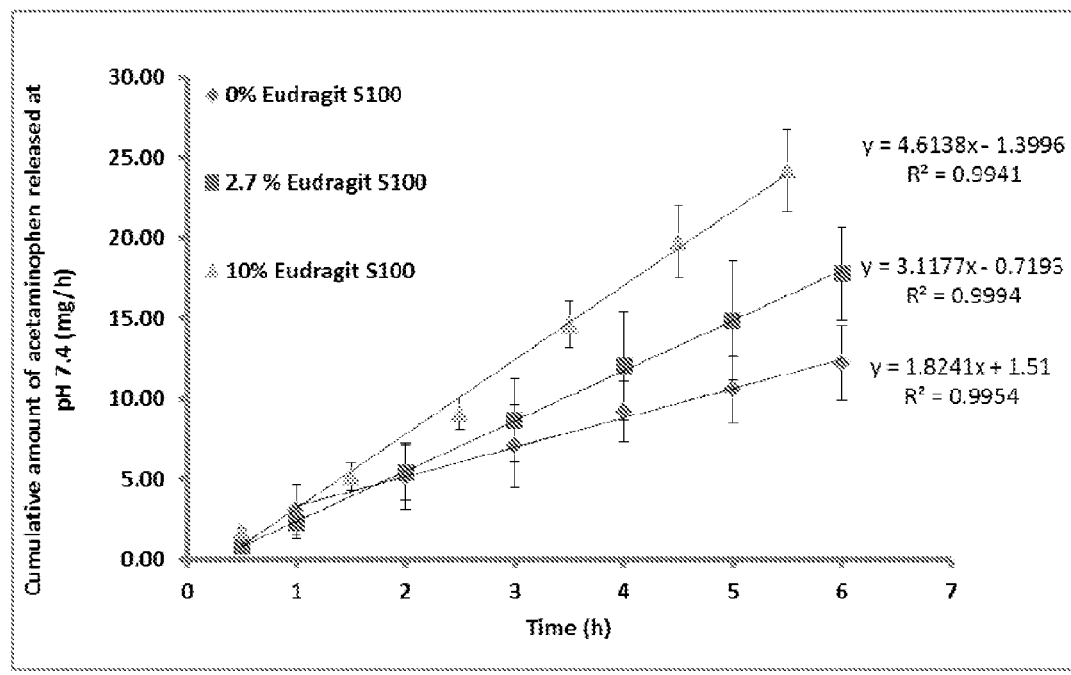
FIG. 12 depicts the release profiles of acetaminophen from cellulose:Eudragit S100 (100:0, 97.3:2.7 and 90:10% w/w) capsule shells in pH 7.4 phosphate buffer solution.

Cellulose, cellulose-Eudragit (90:10) and cellulose: Eudragit (90:10%, w/w) capsule shells (shell thickness~0.08 mm) were prepared according to Example 2. The dissolution test was carried out in pH 7.4 phosphate buffer (900 mL) for 5 h at 37±0.5° C. and 100±2 r.p.m. using a Hansen Research USP II basket apparatus (Hansen Research Corp., Chatsworth, Calif.). The amount of drug released was determined by HPLC according to the method described above. FIG. 12 compares the release results from the three capsule systems. The steady-state release rates calculated were 1.8, 3.1 and 4.6 mg/h, respectively.

We claim:

1. A pharmaceutical dosage form comprising
   (a) a capsule shell comprising regenerated cellulose;
   (b) one or more pharmaceutically active agents disposed within the capsule shell; and
   (c) optionally, a pharmaceutically acceptable formulation agent disposed within the capsule shell, wherein the amount of regenerated cellulose in the capsule shell is about 50% (w/w) or more of the capsule shell, and wherein the regenerated cellulose is present in the capsule shell in an amount that is effective to render the capsule non-disintegrating and non-dissolving in aqueous medium at a physiological temperature and pH.

2. The pharmaceutical dosage form of claim 1, wherein the capsule shell further comprises a cellulose derivative.

3. The pharmaceutical dosage form of claim 1, wherein the capsule shell further comprises at least one compound selected from coating agents, polymers, copolymers, colorants, or plasticizers, or any combination thereof.

4. The pharmaceutical dosage form of claim 1, wherein the capsule shell has at least one layer consisting essentially of regenerated cellulose.

5. The pharmaceutical dosage form according to claim 1, wherein the capsule shell consists essentially of regenerated cellulose.

6. The pharmaceutical dosage form of claim 1, wherein the capsule shell further comprises one or more capsule shell permeability modifiers.

7. The pharmaceutical dosage form of claim 1, wherein the capsule shell further comprises one or more capsule shell porosity modifiers.

8. The pharmaceutical dosage form of claim 1, wherein the release profile of the dosage form in aqueous medium exhibits a zero-order release rate at a physiological pH and temperature.

9. The pharmaceutical dosage form according to claim 1, wherein the capsule shell is prepared by a method comprising
   (a) providing a methylolcellulose solution; and
   (b) forming the capsule shell from the methylolcellulose solution.

10. The pharmaceutical dosage form of claim 9, wherein providing the methylolcellulose solution comprises
    (a1) providing a source of cellulose; and
    (a2) treating the cellulose with paraformaldehyde in anhydrous polar aprotic solvent under conditions suitable to form the methylolcellulose solution.

11. The pharmaceutical dosage form of claim 9, wherein the forming step (b) comprises contacting the methylolcellulose solution with a pin structure and removing the pin structure from the methylolcellulose solution for a time and under conditions that are effective to form a methylolcellulose coating on the pin structure, and wherein the pin structure comprises dimensions that correspond to a capsule size of about size 5 to about size 000.

12. The pharmaceutical dosage form of claim 9, wherein the forming step (b) comprises forming a layer of methylolcellulose, then converting the methylolcellulose to regenerated cellulose by exposing it to water.

13. The pharmaceutical dosage form of claim 1, wherein the release profile of the dosage form in aqueous medium exhibits an apparent zero-order release rate at a physiological pH and temperature.

14. The pharmaceutical dosage form of claim 1, wherein the release profile of the dosage form in aqueous medium exhibits a first order release rate at a physiological pH and temperature.

15. The pharmaceutical dosage form of claim 1, wherein the amount of regenerated cellulose in the capsule shell is more than about 80% (w/w) of the capsule shell.

16. The pharmaceutical dosage form of claim 15, wherein the capsule shell has a thickness in the range of 0.07 mm to 0.1 mm.

17. The pharmaceutical dosage form of claim 15, wherein the capsule shell has a thickness in the range of 0.053 mm to 0.1 mm.

18. The pharmaceutical dosage form of claim 1, wherein the amount of regenerated cellulose in the capsule shell is more than about 90% (w/w) of the capsule shell.

19. The pharmaceutical dosage form of claim 1, wherein the capsule shell has a thickness in the range of 0.07 mm to 0.1 mm.

20. The pharmaceutical dosage form of claim 1, wherein the capsule shell has a thickness in the range of 0.053 mm to 0.1 mm.

21. The pharmaceutical dosage form of claim 1, wherein the capsule shell has a capsule size in the range of about size 5 to about size 000.

22. The pharmaceutical dosage form of claim 21, wherein the capsule shell has a thickness in the range of 0.053 mm to 0.1 mm.

23. The pharmaceutical dosage form of claim 1, wherein the pharmaceutically acceptable formulation agent is disposed within the capsule shell.

* * * * *